(12) United States Patent
Ettrup et al.

(10) Patent No.: US 11,134,892 B2
(45) Date of Patent: *Oct. 5, 2021

(54) OEDEMA TREATMENT AND MONITORING SAME

(71) Applicant: Specialbandager.DK A/S, Bagsværd (DK)

(72) Inventors: Jens Ettrup, Bagsværd (DK); Henrik Harboe, Fårevejle (DK)

(73) Assignee: Specialbandager.dk A/S, Bagsvaerd (DK)

( * ) Notice: Subject to any disclaimer, the term of this patent is extended or adjusted under 35 U.S.C. 154(b) by 414 days.

This patent is subject to a terminal disclaimer.

(21) Appl. No.: 16/068,800

(22) PCT Filed: Jan. 13, 2017

(86) PCT No.: PCT/DK2017/050005
§ 371 (c)(1),
(2) Date: Jul. 9, 2018

(87) PCT Pub. No.: WO2017/121435
PCT Pub. Date: Jul. 20, 2017

(65) Prior Publication Data
US 2019/0015042 A1  Jan. 17, 2019

(30) Foreign Application Priority Data

Jan. 13, 2016 (DK) .............................. PA201670015

(51) Int. Cl.
*A61B 5/00* (2006.01)
*A61B 5/107* (2006.01)
(Continued)

(52) U.S. Cl.
CPC .............. *A61B 5/4878* (2013.01); *A61B 5/01* (2013.01); *A61B 5/0537* (2013.01); *A61B 5/107* (2013.01);
(Continued)

(58) Field of Classification Search
CPC . A61B 5/0022; A61B 5/02055; A61B 5/1118; A61B 5/002; A61B 5/0008;
(Continued)

(56) References Cited

U.S. PATENT DOCUMENTS 5,086,781 A * 2/1992 Bookspan ............ A61B 5/4869
600/547
5,769,809 A * 6/1998 Witzel .................. A61F 2/7812
602/26
(Continued)

FOREIGN PATENT DOCUMENTS

CN    101039641 A    9/2007
CN    101087998 A    12/2007
(Continued)

OTHER PUBLICATIONS

La'tayah Christie-Ornstrup: "Edema Stacking", Jan. 28, 2013, XP055355372, Retrieved from the Internet: URL:http://www.edema.dk/wp-content/uploads/2013/01/Edema_Stockingresearchers.pdf (retrieved on Mar. 15, 2017).
(Continued)

*Primary Examiner* — May A Abouelela
(74) *Attorney, Agent, or Firm* — Dinsmore & Shohl LLP

(57) ABSTRACT

The present disclosure relates in general to methods for treating oedema and methods for monitoring the effect of the treatment. More specifically, the present disclosure includes measurement of a measure of a circumference of a body
(Continued)

part, wherein the body part may have swelled, such that it for example can be observed whether the swelling decreases or increases.

12 Claims, 22 Drawing Sheets

(51) Int. Cl.
*A61B 5/01* (2006.01)
*A61B 5/0537* (2021.01)
*A61F 13/06* (2006.01)
(52) U.S. Cl.
CPC .......... *A61B 5/1075* (2013.01); *A61B 5/4848* (2013.01); *A61B 5/6802* (2013.01); *A61F 13/06* (2013.01); *A61B 2560/0242* (2013.01); *A61B 2562/0219* (2013.01)
(58) Field of Classification Search
CPC ......... A61B 5/1116; A61B 5/01; A61B 5/053; A61B 5/6807; A61B 5/6824; A61B 5/7275; A61B 5/6804; A61B 5/6831; A61B 5/6801; A61B 5/6802; A61B 5/0205; A61B 5/4875; A61B 5/6823; A61B 5/4878; A61B 5/107; A61B 5/0537; A61B 5/1075; A61B 5/4848; A61B 2560/0242; A61B 2562/0219; A61F 13/06
USPC .......................... 600/300, 390, 547, 587, 595
See application file for complete search history.

(56) References Cited

U.S. PATENT DOCUMENTS

| 5,891,059 | A | * | 4/1999 | Anderson | A61B 5/107 600/561 |
|---|---|---|---|---|---|
| 6,409,662 | B1 | * | 6/2002 | Lloyd | A61B 5/1073 600/300 |
| 6,714,813 | B2 | * | 3/2004 | Ishigooka | A61B 5/0537 600/300 |
| 7,801,598 | B2 | * | 9/2010 | Zhu | A61B 5/022 600/547 |
| 8,827,930 | B2 | * | 9/2014 | Wekell | A61B 5/0205 600/587 |
| 8,948,839 | B1 | | 2/2015 | Longinotti-Buitoni et al. | |
| 2001/0020138 | A1 | * | 9/2001 | Ishigooka | A61B 5/0537 600/547 |
| 2003/0120170 | A1 | * | 6/2003 | Zhu | A61B 5/4869 600/547 |
| 2004/0044290 | A1 | * | 3/2004 | Ward | A61B 5/022 600/490 |
| 2004/0186395 | A1 | * | 9/2004 | Vastano | A61B 5/1073 600/587 |
| 2006/0084855 | A1 | * | 4/2006 | Teschner | A61B 5/0536 600/390 |
| 2008/0306401 | A1 | * | 12/2008 | Okura | A61B 5/0537 600/547 |
| 2009/0018464 | A1 | * | 1/2009 | Watanabe | A61B 5/0537 600/547 |
| 2009/0318779 | A1 | * | 12/2009 | Tran | A61B 5/7267 600/301 |
| 2012/0172747 | A1 | * | 7/2012 | Fukuda | A61B 5/4872 600/547 |
| 2012/0179067 | A1 | * | 7/2012 | Wekell | A61B 5/4848 600/587 |
| 2013/0338472 | A1 | * | 12/2013 | Macia Barber | A61B 5/6804 600/388 |
| 2014/0052028 | A1 | * | 2/2014 | Wright | A61B 5/1075 600/592 |
| 2014/0275857 | A1 | * | 9/2014 | Toth | A61B 5/083 600/301 |
| 2014/0296749 | A1 | | 10/2014 | Reid, Jr. et al. | |
| 2014/0343391 | A1 | * | 11/2014 | Korkala | A61B 5/0408 600/393 |
| 2015/0143601 | A1 | | 5/2015 | Longinotti-Buitoni et al. | |
| 2015/0201856 | A1 | * | 7/2015 | Stork | A61B 5/01 600/384 |
| 2016/0015297 | A1 | * | 1/2016 | Strauss | A61B 5/1073 600/587 |
| 2017/0000360 | A1 | * | 1/2017 | Breen | A61B 5/11 |
| 2017/0079868 | A1 | * | 3/2017 | Reid, Jr. | D04B 1/265 |

FOREIGN PATENT DOCUMENTS

| CN | 101309658 A | 11/2008 |
|---|---|---|
| CN | 201469257 U | 5/2010 |
| CN | 105025937 A | 11/2015 |
| JP | 2013508002 A | 3/2013 |
| JP | 2015532841 A | 11/2015 |
| KR | 20080073531 A | 8/2008 |
| KR | 101573043 B1 | 12/2015 |
| WO | 0049968 A2 | 8/2000 |
| WO | WO-2004/093763 A1 | 11/2004 |
| WO | WO-2004/100784 A2 | 11/2004 |
| WO | 2008089787 A1 | 7/2008 |
| WO | WO-2013/179670 A1 | 12/2013 |
| WO | 2014206379 A1 | 12/2014 |
| WO | WO-2015/002267 A1 | 1/2015 |
| WO | 2015077838 A1 | 6/2015 |
| WO | 2015156174 A1 | 10/2015 |

OTHER PUBLICATIONS

Le Cai et al.: "Super-stretchable, Transparent Carbon Nanotube-Based Capacitive Strain Sensors for Human Motion Detection", Scientific Reports, vol. 3, No. 1, Oct. 25, 2013, XP055600771.
Merritt C R et al.: "Textile-Based Capacitive Sensors for Respiration Monitoring", Ieee Sensors Journal, Ieee Service Center, New York, NY, US, vol. 9, No. 1, Jan. 1, 2009, p. 71-78, XP011239808.

\* cited by examiner

OEDEMA TREATMENT AND MONITORING SAME

The present invention relates to treatment of oedema as well as to the monitoring of the treatment and garment for use in the treatment.

BACKGROUND OF INVENTION

The present disclosure relates in general to methods for treating oedema and methods for monitoring the effect of the treatment. More specifically, the present disclosure includes measurement of a measure of a circumference of a body part, wherein the body part may have swelled, such that it for example can be observed whether the swelling decreases or increases.

BACKGROUND OF INVENTION

Oedema may be caused by several underlying diseases. The most common forms are oedema due to venous insufficiency and lymphoedema.

Oedema caused by venous insufficiency are typically seen in the legs, and are often seen in both legs.

Lymphoedema may manifest as swelling in any body part, such as arms, legs, trunk, head and neck, and is normally found in individuals having gone through surgery or radiotherapy for cancer.

Oedema is the result of accumulation of fluid in the tissue spaces, and may produce significant physical and psychological morbidity. Pain and discomfort are frequent symptoms and increased susceptibility to ulcers and skin infections can result in frequent hospitalization and long term dependency on antibiotics. Oedema due to venous insufficiency and lymphoedema is a chronic condition, that may be alleviated by appropriate management. If chronic oedema is not treated properly as time progresses the fluid and waste products in the tissues can cause tissue thickening and fibrosis (excessive fibrous tissue). The tissues become hard and the swelling does not reduce on limb elevation.

One way of managing chronic oedema is to reduce swelling through a combination of compression, for example using bandage or compression garment and exercise with or without lymphatic massage.

Many compression systems are available. To choose an appropriate compression product for a patient, in particularly a patient with leg ulcers requires a thorough understanding of the various products. However, this choice can be difficult because of lack of standardized compression classifications, confusion over terminology, and lack of evidence as to which type of compression system is most effective.

SUMMARY OF INVENTION

The present invention relates to methods for monitoring the treatment of oedema, in particularly chronic oedema, in order to allow a physician in collaboration with the patient to be able to select an optimal compression bandage or garment, to monitor the effect of the bandage or garment, and to support decisions on when to change the bandage or garment.

Accordingly, in one aspect the invention relates to a method for determining the efficiency of a treatment of oedema in a body part by compression bandaging, said method comprising applying said bandaging to said body part,
applying at least one sensor to said body part under, within or over said bandaging, each sensor comprising
 one or more electrically conducting layer(s) on or around at least a part of said body part, wherein the electrically conducting layer(s) is/are stretchable;
 a measuring unit that is electrically connected to the one or more electrically conductive layer(s), wherein the measuring unit is configured for measuring an electric property related to the one or more electrically conducting layer(s), and the electric property is related to the measure of the circumference of the body part;
registering a plurality of measures of the circumference of the body part during a predetermined period,
determining that the treatment is efficient when the circumference of the body part has decreased to below a predetermined cutoff value and/or the decrease of the circumference of the body part is above a predetermined cutoff value after said predetermined period.

In addition, the invention relates to a method for treatment of chronic oedema, said treatment comprising a method for determining the efficiency of maintenance compression treatment of chronic oedema in a body part, said method comprising applying a compression bandage or garment to said body part,
applying at least one sensor to said body part under, within or over said bandage or garment, each sensor comprising
 one or more electrically conducting layer(s) on or around at least a part of said body part, wherein the electrically conducting layer(s) is/are stretchable;
 a measuring unit that is electrically connected to the one or more electrically conductive layer(s), wherein the measuring unit is configured for measuring an electric property related to the one or more electrically conducting layer(s), and the electric property is related to the measure of the circumference of the body part;
registering a plurality of measures of the circumference of the body part during a predetermined period,
determining that the treatment is efficient when the circumference of the body part varies within a predetermined interval during said predetermined period.

In yet another aspect the invention relates to a method for determining the lifetime end of a compression bandage or garment for bandaging a body part, said method comprising applying said bandage or garment to said body part,
applying at least one sensor to said body part under, within or over said bandage or garment, each sensor comprising
 one or more electrically conducting layer(s) on or around at least a part of said body part, wherein the electrically conducting layer(s) is/are stretchable;
 a measuring unit that is electrically connected to the one or more electrically conductive layer(s), wherein the measuring unit is configured for measuring an electric property related to the one or more electrically conducting layer(s), and the electric property is related to the measure of the circumference of the body part;
registering a plurality of measures of the circumference of the body part during a predetermined period,
determining that that the lifetime of the compression bandage or garment has ended when the circumference of the body part increases above a predetermined cutoff and/or the increase is above a predetermined cutoff during said predetermined period.

The invention also relates to a method for determining the risk of skin infection in an individual having a bandaged body part, said method comprising
 applying said bandaging to said body part,
 applying a sensor to said body part under, within or over said bandaging, said sensor comprising
  one or more electrically conducting layer(s) on or around at least a part of said body part, wherein the electrically conducting layer(s) is/are stretchable;
  a measuring unit that is configured for measuring the temperature and/or moisture of the body part;
 registering a plurality of said measures of the body part during a predetermined period,
 determining that there is a risk of skin infection under the bandage when the measure of temperature and/or moisture increases above a predetermined cutoff during said predetermined period.

In another aspect the electrically conducting layers are retractable upon a signal and may be used for active compression, and accordingly the invention relates to a method for treating oedema of a body part, comprising
 applying a bandage to said body part,
 applying an actuatable sensor to said body part under, within or over said bandaging, said sensor comprising
  one or more electrically conducting layer(s) on or around at least a part of said body part, wherein the electrically conducting layer(s) is/are stretchable, and wherein the electrically conducting layer(s) is/are retractable upon a signal applied to the layer(s);
  a measuring unit that is electrically connected to the one or more electrically conductive layer(s), wherein the measuring unit is configured for measuring an electric property related to the one or more electrically conducting layer(s), and the electric property is related to the measure of the temperature and/or moisture of the body part;
 registering a plurality of said measures of the body part during a predetermined period,
 actuating the sensor thereby retracting the sensor when the circumference of the body part increases above a predetermined cutoff after said predetermined period.

Furthermore, the information obtained through monitoring the efficiency of a compression treatment may be used for designing optimized compression garments, and consequently the invention relates to a method for designing a compression garment for the maintenance treatment of chronic oedema in a body part, said method comprising
 obtaining said plurality of measures of the circumference of the body part for each of at least two sensor positions according to the method as defined above, for at least one predetermined period,
 determining the compression requirements for each segment of the body part corresponding to the sensor positions,
 designing a compression stocking based on the determined compression requirements.

And the invention also relates to the optimized compression garment as well.

A further aspect relates to a method for identifying a treatment regimen for an individual, comprising the steps of: applying a bandaging to said body part, applying at least one sensor to said body part under, within or over said bandaging, each sensor comprising: one or more electrically conducting layer(s) on or around at least a part of said body part, wherein the electrically conducting layer(s) is/are stretchable; a measuring unit that is electrically connected to the one or more electrically conductive layer(s), wherein the measuring unit is configured for measuring an electric property related to the one or more electrically conducting layer(s), and the electric property is related to the measure of the circumference of the body part; registering a plurality of measures of the circumference of the body part during a predetermined period, registering a plurality of measures of the movement of the body part during the predetermined period, and determining the treatment regimen from said plurality of measures of the movement of the body part.

DEFINITIONS

Figure 1:
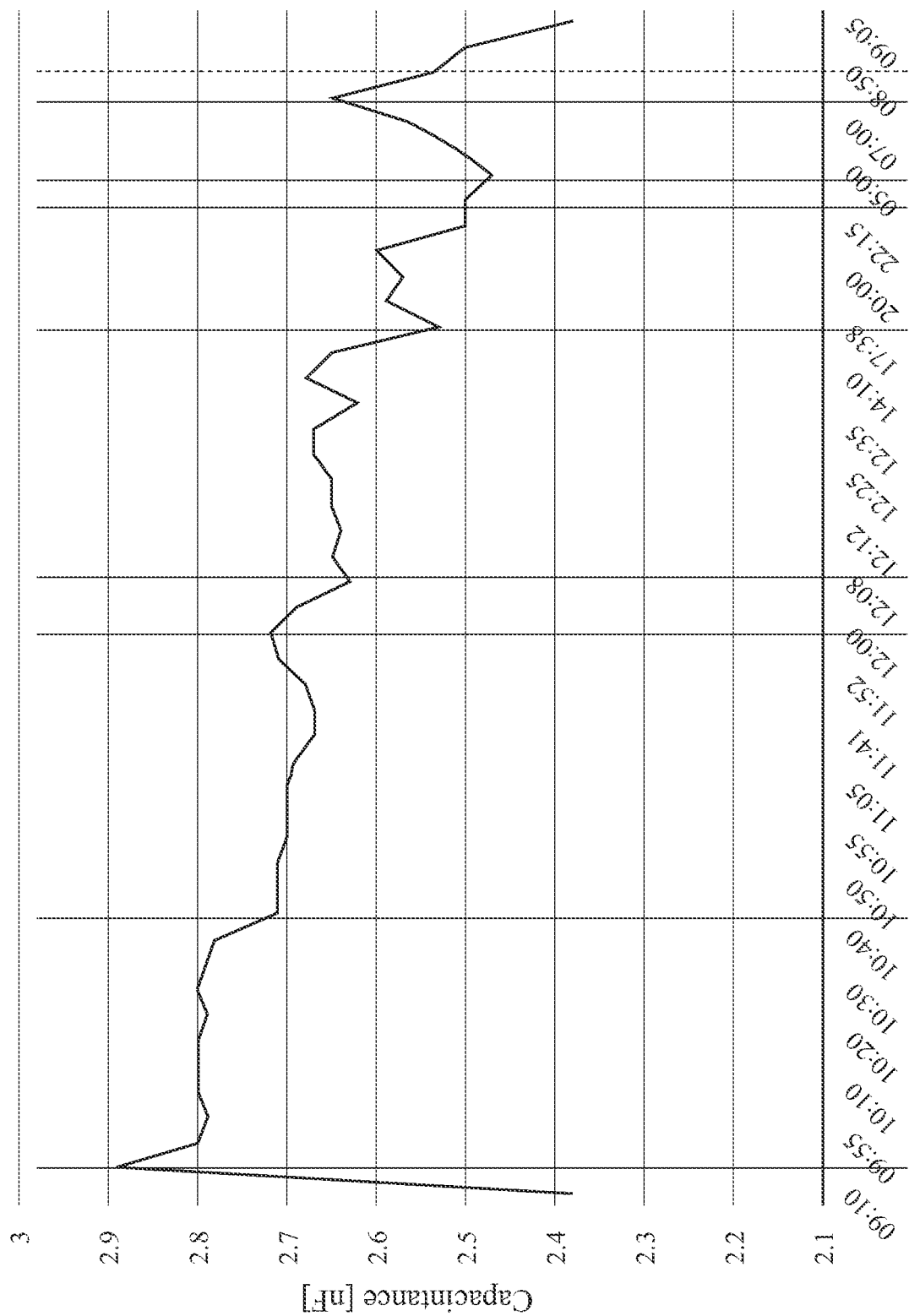
FIG. 1 shows how the electric property, related to the circumference of a leg, in a first position B, changes with time. A time period of approximately 24 hours is shown along the horizontal axis, and the electric property, the capacitance, is shown along the vertical axis. Several measurement points have been indicated along the 24 time period. First is indicated a first measurement 1 where the bandage is applied to the leg. A second measurement 2 is where the patient changes from sitting to walking. A third measurement 3 is where before the bandage is re-applied to the leg and measurement 4 is after the bandage has been re-applied. Measurement 5 is where the patient has the leg in a horizontal position. Measurement 6 is where the patient goes to bed and measurement 7 is where the patient wakes up. At measurement 8, the patient drives a car. At the end, at measurement 9, the measurements are done.

The following definitions are used throughout the text:

Oedema means the swelling of a body part, and the term "Oedema" covers oedema due to venous insufficiency as well as lymphoedema.

Compression bandage means layers of bandage to be wrapped around a body part.

Compression garment means a garment fit to a body part to be treated and comprises compression stockings for legs as well as arms, compression gloves, compression vests, and compression masks.

Compression treatment is divided into initial treatment for reducing a swelling and maintenance treatment for inhibiting swelling in an individual suffering from oedema.

DETAILED DESCRIPTION OF THE INVENTION

The treatment of oedema, in particularly chronic oedema, such as oedema caused by venous insufficiency or lymphoedema, is primarily compression of the oedematous body part through the use of compression bandages and compression garments.

Typically the treatment may be divided into an initial compression treatment wherein the swelling is reduced as much as possible, and a maintenance compression treatment performed to reduce the risk for a new swelling.

Compression bandages and compression garments are meant to be worn twenty four hours a day, or at least the waking hours, every day to maintain oedema reduction and must be replaced on a regular basis. Compression garments may be custom-fit or purchased in over-the-counter, i.e. in standard sizes. Some people will require custom-made compression garments and it is important that these garments fit correctly.

Compression bandage or garment materials are typically characterized into elastic, long-stretch, inelastic, or short-stretch material. The terms elastic and long-stretch (elastic/long-stretch) bandages are often used synonymously, as are inelastic and short-stretch (inelastic/short-stretch) bandages. Extensibility differs markedly between these two basic types. Extensibility refers to the degree to which the bandage can be stretched when pulled. Generally, an elastic/long-stretch bandage has a maximal extensibility greater than 100%, whereas an inelastic/short-stretch bandage has a maximal extensibility of less than 100%. However, even material within the same category, for example inelastic material, from different commercial providers may have different degrees of elasticity and durability.

As discussed below the two different types of compression bandage and garment material may be suitable for different types of oedema and patients.

Gradient compression, ie. a pressure gradient decreasing towards the heart is the basic principle for compression therapies. Roughly 60% to 80% of the body's total blood volume resides in the venous circulation. During walking or weight shifting, calf-muscle contraction is the primary means of returning blood to the heart through the veins. Short-stretch bandages create an external force against calf-muscle contraction. They cause generation of inward pressure because they don't allow calf muscles to bulge outward when they contract and shorten. This force compresses and pumps the veins, propelling blood toward the heart; graduated compression of bandages (more pressure at the ankle than calf) prevents backward blood regurgitation through incompetent veins. This is called working pressure. Thus, short-stretch compression treatment cause high working pressure.

In contrast, long-stretch bandages stretch as oedema increases. They also provide little resistance to calf-muscle contraction. Therefore, they have low working pressure, don't promote the calf-muscle pump, and provide poor oedema containment. However, initially long-stretch bandages may provide a suitable treatment in the initial phase of treating oedema.

Treatment of oedema often involves general exercise, such as walking, or specific therapeutic exercises while compression bandaging is worn, because it aids in the elimination of excess fluid.

Compression Bandage and Compression Garment

As defined above compression bandage is a bandage consisting of one or more layers of bandage wrapped around the body part, optionally in combination with padding. Compression bandage is normally used in the initial phase of oedema treatment in order to decrease the swelling. Compression bandage may be re-applied regularly, such as at least every third day.

Also, as defined above compression garment may be provided for any body part. The majority of the compression garments are compression stockings. In the following stockings are discussed in further details, however the discussion applies equally well to the other types of garments.

Compression stockings are produced by one of two different processes, either by flat-knit processes or by circular knit processes.

Compression stockings produced by flat-knit machines are knit row by row, following a knitting pattern. Flat-knit stockings can be produced in almost unlimited shapes and sizes in accordance with the presented anatomical shape, and can also be made to fit even extreme deformities. The flat-knit process is suitable for custom-made products, especially for higher compression classes. Because of their perfect fit, the stockings are able to deliver an exact level of compression, as well as a pressure gradient, even for extreme body shapes. Flat-knit stockings are normally thicker and have a seam.

Circular-knit compression stockings, like regular ladies' nylons, are knitted on a cylinder and have no seam. The same number of loops per row is normally used over the whole length of the stocking. Circular knitting is primarily suitable for manufacturing support stockings, and stockings for prophylaxis. Seamless circular-knit stockings can be made finer/thinner and cosmetically more attractive than stockings produced by flat-knitting.

Independent of choice of compression bandage or compression garment, the bandage or garment has only limited durability, even if treated with utmost care. After approximately 6 months it wears out and loses its compression effectiveness.

However, there may also be a need for a change of compression stocking earlier if the compression treatment has been so efficient that the swelling has been be reduced to the point that the old one is too wide now.

Determining the Efficiency of a Treatment

In one aspect the invention relates to a method for determining the efficiency of a treatment of oedema in a body part, in particularly the initial treatment wherein a swelling is to be reduced. The method comprises applying a compression bandage or garment and furthermore applying at least one sensor as described in detail below to said body part. The sensor may be applied below, within or on the compression bandage or garment, as is suitable for the patient to be treated and the bandage and garment.

The method may be carried out using one sensor per body part to be treated, however it is normally preferred that at least two sensors are used, and more preferred that at least three sensors are used in order to obtain the information necessary to determine the efficiency of the treatment. The sensors are preferably positioned at the standard measurement positions used in the art. Standard positions for measuring are shown in FIG. 1 for the leg, and standard positions for the leg as well as other body parts may be found in text books and guidelines for clinicians treating oedema.

By use of the sensor, a plurality of measures of the circumference of the body part is measured during a predetermined period. The predetermined period is any suitable period in view of the phase of the treatment and the condition of the patient to be treated. Normally, the predetermined period is at least 12 hours, such as at least 24 hours, such as at least 2 days, such as at least 3 days.

The efficiency of the treatment may also be determined taking into account the exercises performed by the patient. In a preferred embodiment the sensor is capable of providing a measure for the movement of the body part in question. In general, the more a body part is moving the faster a swelling will decrease. Accordingly, the efficiency of the treatment may be a measure of the decrease of swelling in view of any exercise performed. Movements may be measured directly through the sensor as described below, or movements may be measured by any other means, such as a accelerometer, as described below.

Within the predetermined period measurements are performed at regular intervals, preferably several times per hour. In particularly, in order to take into account any movements made by the patient during monitoring, it is preferred to perform measurement at least 4 times per hour, more preferably at least 6 times per hour or 12 times per hour.

After the end of the predetermined period the treatment is determined to be efficient when the circumference of the body part has decreased to below a predetermined cutoff value and/or the decrease of the circumference of the body part is above a predetermined cutoff value.

The cutoff may be a standard cutoff, or may be determined individually in view of the phase of the treatment and the condition of the patient. Typically, the cutoff for the decrease is at least 0.5 cm. to 3 cm per day in the beginning of the treatment to be reduced towards the end of the initial treatment. In another embodiment the cutoff is defined as a percentage decrease such as at least 1% to 6% decrease. Normally, the cutoff is higher the more exercises the patient has performed during the predetermined period.

By performing the method it is possible to evaluate the efficiency of the treatment much earlier than what is obtainable by prior art methods, and furthermore documentation of the treatment is also facilitated by the present method.

In case the treatment has not proved to be efficient, in view of the patient's exercise, changes in the treatment must be considered, such as changing the compression bandage or garment material or, in case of a compression bandage, re-wrapping the bandage.

In another aspect the invention relates to a method for determining the efficiency of maintenance compression treatment of chronic oedema in a body part, ie. after the initial reduction of the swelling in order to prevent a new swelling.

Like the method above, the present method involves applying a compression bandage or garment to said body part, and applying at least one sensor to said body part under, within or over said bandage or garment.

Also, a plurality of measures of the circumference of the body part is measured during a predetermined period, and normally the same frequency of measurements are carried out for the maintenance treatment as for the initial treatment. Furthermore, the number of sensors as well as the position of sensors described above apply equally well in this aspect of the invention.

The maintenance compression treatment is determined to be efficient when the circumference of the body part varies within a predetermined interval during said predetermined period, and does not increase above the interval. The interval is normally a few centimeters, such as about 3 cm, more preferably 2 cm. If a swelling is larger than to be accommodated within said interval, there is a great risk that the compression treatment is not efficient, in particularly if the measurements during the following periods exhibit the same tendency.

Due to the plurality of measurement carried out through the predetermined periods, the method also provides useful information about variations during the day. For patients having leg oedemas and standing a part of the day, as for example school teachers and some craftsmen, the method may provide information as to whether the compression treatment is effective when they are at work, and when they are at home, which may lead to the conclusion that they may need different compression stockings for work and for home.

Furthermore, by monitoring the treatment as described above it is also possible to regulate hospital visits for the patient, in that a patient with an efficiently working compression bandage or garment may not need to visit to the hospital as often as those wherein the swelling does not decrease or indeed increases.

As discussed above compression bandage or garment from different commercial providers exhibit different compression characteristics with respect to elasticity and durability. Compression garments designed to fit the individual patient, whether over-the-counter or customized goods, is worn daily and has to be washed regularly which exerts a certain wear of the garment. Normally a patient has some sets of garment to shift between, however if the garment is financed fully or partly by health care insurance or the like, a patient is normally not granted more than two sets each half year. Accordingly, the durability of the compression characteristics is a very important factor to be considered for the patient, since when the compression characteristics do not fulfil the requirements the patient risks serious side effects in the form of new swelling and subsequent ulcers and infection.

The present invention provides a method for determining when the lifetime has ended or is about to end for a compression garment, ie. when the compression characteristics of the compression garment does not fulfil the requirements for the patient in question, and therefore when it is suitable to acquire new sets of garments.

Therefore, the invention also relates to a method for determining the lifetime end of a compression bandage or garment for bandaging a body part, said method comprising
  applying said bandage or garment to said body part,
  applying at least one sensor to said body part under, within or over said bandage or garment, each sensor comprising
    one or more electrically conducting layer(s) on or around at least a part of said body part, wherein the electrically conducting layer(s) is/are stretchable;
    a measuring unit that is electrically connected to the one or more electrically conductive layer(s), wherein the measuring unit is configured for measuring an electric property related to the one or more electrically conducting layer(s), and the electric property is related to the measure of the circumference of the body part;

registering a plurality of measures of the circumference of the body part during a predetermined period, determining that that the lifetime of the compression bandage or garment has ended when the circumference of the body part increases above a predetermined cutoff and/or the increase is above a predetermined cutoff during said predetermined period.

As discussed above, individuals suffering from oedema are at risk of acquiring an infection of the skin in the oedematous body part. The present invention provides a method for determining the risk of infection, whereby an early warning sign is provided leading to either prevention of the infection or an early treatment. Accordingly, the present invention relates to a method for determining the risk of skin infection in an individual having a bandaged body part, said method comprising applying said bandaging to said body part, applying a sensor to said body part under, within or over said bandaging, said sensor comprising one or more electrically conducting layer(s) on or around at least a part of said body part, wherein the electrically conducting layer(s) is/are stretchable;

a measuring unit that is configured for measuring the temperature and/or moisture of the body part;

registering a plurality of said measures of the body part during a predetermined period, determining that there is a risk of skin infection under the bandage when the measure of temperature and/or moisture increases above a predetermined cutoff during said predetermined period.

The measuring unit configured for measuring the temperature and/or moisture of the body part may be electrically connected to the one or more electrically conductive layer(s), whereby the measuring unit is configured for measuring an electric property related to the one or more electrically conducting layer(s), and the electric property is related to the measure of the temperature and/or moisture of the body part in that the resistivity of a single electrically conducting layer as may be temperature dependent, and by registering the resistivity a measure for the temperature is obtained.

In an alternative, the measuring unit comprises a sensor to measure temperature and/or moisture.

Measuring either the temperature or the moisture under the compression bandage or garment provides the patient and/or the physician with an early sign of suspected infection. By the method according to the invention it is not necessary to remove the bandage or garment to inspect the body part for infection too often, since the risk for infection may be determined while the patient is wearing the bandage or garment. On the other hand, although the patient is wearing the bandage or garment, it is still possible to get an early warning. Normally a temperature rise of from 0.5° C., such as from 1.0° C. is an indicator of infection.

Actuatable Sensor

In yet another aspect of the invention the sensor for measuring changes in the circumference may also be an actuatable sensor capable of retracting as response to a signal, such as an electrical signal. Thereby, the sensor(s) may also be an active part of the treatment of oedema, and consequently, the invention further relates to a method for treating oedema of a body part, comprising applying a bandage to said body part, applying an actuatable sensor to said body part under, within or over said bandaging, said sensor comprising one or more electrically conducting layer(s) on or around at least a part of said body part, wherein the electrically conducting layer(s) is/are stretchable, and wherein the electrically conducting layer(s) is/are retractable upon a signal applied to the layer(s);

registering a plurality of said measures of the body part during a predetermined period, actuating the sensor thereby retracting the sensor when the circumference of the body part increases above a predetermined cutoff after said predetermined period.

In a preferred embodiment the method also includes a control unit and a transmitting unit, whereby the control unit is configured to control the length of the one or more electrically conducting layer(s) along the longitudinal axis, for example by receiving the measure of the circumference of the body part directly from the transmitting unit.

The one or more electrically conducting layer(s), described in detail below, may be configured as an actuator, such that when the control unit receives input, for example based on the measure of the circumference of the body, the control unit may send an electrical signal to the one or more electrically conducting layer(s) to cause a retraction of the layer(s).

Thus, by having the control unit, the present invention provides for a feed-back mechanism based, i.e. treatment that is based on tightening the first elastic support material further to the body part when it receives instructions based on output from the measuring unit. In other words, the present invention may provide an automatic and self-adaptable support material, for example such as a bandage and/or a compression garments.

Preferably, the method includes at least two actuatable sensors, whereby the actuation of the sensor is performed individually for each sensor. In one embodiment one sensor may be retracted to one extent and the other retracted to another extent or not retracted at all to accommodate that a swelling may occur locally in the body part.

The retraction, independent of the number of sensors, may be a permanent retraction until the measurements performed may indicate a need for either a relaxation or a further retraction. In another embodiment, or the actuatable sensor performs a pulsating movement of repetitive retractions and relaxations in order to perform an intermittent pumping therapy to provide a lymph drainage. In the latter embodiment it is preferred if two or three sensors take part in the pumping therapy.

Design of Compression Garment

In yet another aspect of the invention there is provided a method for designing a compression garment based on the results obtained from the monitoring of the efficiency of the treatment. From the information obtained from an individual patient it is possible to design a compression garment having the exact compression characteristics that may be required to treat the patient's oedema in the most efficient way. For example, it may be experienced during the monitoring that more compression forces are required in some segments of the body part and less in order segments of the body part. Today compression garments, in particularly compression stockings, are provided with the same elasticity throughout the garment, and the only methods for individualizing the garment is the adaptation of the width of various segments of the garment.

Accordingly, in one aspect the invention relates to a method for designing a compression garment for the maintenance treatment of chronic oedema in a body part, said method comprising obtaining said plurality of measures of the circumference of the body part for each of at least two sensor positions according to the method as defined above, for at least one predetermined period, determining the compression requirements for each segment of the body part corresponding to the sensor positions, designing a compression stocking based on the determined compression requirements.

Compression stockings may be designed to have at least two stocking segments, and more preferably at least three stocking segments, corresponding to the measurement positions. Each stocking segment may be designed to have different compression characteristics. One example is a stocking capable of increasing the pressure just above the ankle, another example is a stocking capable in decreasing the pressure at the top of the stocking, or a combination thereof.

Preferably, the information obtained from monitoring the efficiency of one compression garment may be transferred directly to the production line for an individualized stocking to take into account the need for individualized compression characteristics in various segments of a stocking.

Furthermore, the invention relates to a compression stocking for maintenance compression treatment comprising at least a first segment and a second segment, wherein the compression characteristic in the first segment is different from the compression characteristic in the second segment as discussed above.

Determining a Treatment Regimen

In a further aspect, the invention relates to a method for determining a treatment regimen. The method comprises the steps of applying a bandaging to said body part, applying at least one sensor to said body part under, within or over said bandaging, each sensor comprising, one or more electrically conducting layer(s) on or around at least a part of said body part, wherein the electrically conducting layer(s) is/are stretchable; a measuring unit that is electrically connected to the one or more electrically conductive layer(s), wherein the measuring unit is configured for measuring an electric property related to the one or more electrically conducting layer(s), and the electric property is related to the measure of the circumference of the body part; registering a plurality of measures of the circumference of the body part during a predetermined period, registering a plurality of measures of the movement of the body part during the predetermined period, and determining the treatment regimen from said plurality of measures of the movement of the body part.

By determining the treatment regimen as based on the movement of the body part, a feedback of the individual's behavior may be possible. Such feedback may provide for an optimal treatment of the individual.

In one embodiment, the plurality of measures of the movement of the body part is measured using an accelerometer. The accelerometer may for example be attached to the body part of the individual.

In another embodiment, the plurality of measures of the movement of the body part is measured using the sensor, for example, as an alternative to the accelerometer.

In another alternative embodiment, the accelerometer is integrated into the sensor.

In preferred embodiments, the treatment regimen relates to an activity of the individual. For example, readings from the accelerometer and/or the sensor may be used to notify the individual what is best for him/her. For example, the individual may be notified that optimal treatment is enabled if the individual plans to cycle or walk for half an hour or so within the next 4 hours. The notifications as related to the activity of the individual may be based on the individual's present activity and/or a logged activity. For example, the accelerometer and/or the sensor may be configured for determining whether the individual is inactive, by such as sleeping or active, such as walking, running, or cycling. Based on the activities, the individuals may also be rated according to a type of the individual. For example, a very active person may be rated as a person 1, and a very inactive person may be rated as a person 3. Based on the activity and/or the type of individual, the individual may be notified of a treatment regimen that is best suited for the individual. In this regard, a personalized treatment is achieved.

Preferably, the treatment regimen is displayed to the individual on a display, such as a mobile phone, a tablet, or a computer.

According to most of the aspects, a sensor is applied to the body part. In most preferred embodiments of these aspect, the step of applying at least one sensor to said body part is followed by determining an amount of stretch of the sensor, such that if the amount of stretch is below a predetermined amount, a warning related to under-stretching is displayed to the individual on a display, and if the amount of stretch is above a predetermined amount, a warning related to over-stretching is displayed to the individual on a display. Hereby is provided that the sensor that provides for the most optimal treatment is correctly applied to the body part.

Computer Implemented Method

The methods described above may also be provided as computer implemented methods for managing treatment of oedema. Accordingly, in any of the methods described above the method may further include the steps of:

in a computer receiving a plurality of measures of the circumference of the body part, wherein each of said plurality of measures are either absolute values of the circumference of the body part or a delta value describing a difference to a former value;

determining whether the circumference of the body part is above a predetermined cutoff; and returning an indicator to an indicator system, wherein the indicator indicates whether the circumference is above the predetermined cutoff.

The indicator may be any type of relevant information, such as a visual alarm on a computer screen if the circumference changes to a value above a predetermined cutoff. Thereby, the physician and other professionals treating the patient are helped in identifying the patients that may need attention, and do not spend time on patients who are performing well. The indicator system may likewise be available to the patient in order to monitor his or her own treatment.

Thereby, the methods according to the present invention may be included in telemedicine methods, where the professionals treating the patient are positioned far from the patient and at least initial information is provided in a combination of automatic information and digital communication with the patient, being by telephone, through the computer or as emails.

Sensor

The sensor according to the invention comprises
one or more electrically conducting layer(s) on or around at least a part of said body part, wherein the electrically conducting layer(s) is/are stretchable; and
a measuring unit that is electrically connected to the one or more electrically conductive layer(s), wherein the measuring unit is configured for measuring an electric property related to the one or more electrically conducting layer(s), and the electric property is related to the measure of the circumference of the body part.

Preferably, the sensor comprises a first elastic support material configures for being place around and/or on the body part and/or on a second elastic support material in contact with the body part. Preferably, the one or more electrically conducting layer(s) is(are) in contact with said first elastic support material.

Electrically Conducting Layer(s)

The one or more electrically conductive layer(s) may be made from a material having a resistivity which is less than $10^{-2}$ Ωcm such as less than $10^{-4}$ Ωcm.

The one or more electrically conductive layer(s) may preferably be made from a metal or an electrically conductive alloy, e.g. from a metal selected from a group of silver, gold and nickel. Alternatively other suitable metals or electrically conductive alloys may be chosen.

The one or more electrically conductive layer(s) may be electrical tape, such as made of conductive acrylic with for example Nickel plated carbon scrim. The tape may be adhesive.

The one or more electrically conductive layer may have a thickness in the range of 0.01 μm to 0.1 μm, such as in the range of 0.02 μm to 0.1 μm, such as in the range of 0.08 μm to 0.1 μm.

A first conductor may be attached to the one or more electrically conductive layer(s) in a first connection point. The conductor may be formed as an elongated body like a traditional wire or cable. In another embodiment, the conductors may be formed as pouches being circular, oval, or of another shape suitable for establishing the electrically communication with electrodes. The conductor may be highly elastically deformable such that the length of the conductor may be varied, or the conductors may at least be flexibly bendable.

The one or more electrically conducting layer(s) may have an electrically conducting layer length that, in a relaxed state, is less than 90% relative to the elastic support length, such as less than 75%, such as less than 60%, such as less than 50%, such as less than 40%, such as less than 30%, such as less than 20%, or such as less than 10%. This may reduce cost of the electrically conducting layer length, and still provide a measure of the circumference of the body part.

The one or more electrically conducting layer(s) may have an electrically conducting layer length, in a relaxed state, between 2 cm and 85 cm.

The one or more electrically conducting layer(s) may have an electrically conducting layer width that, in a relaxed state and along the vertical axis, is between 2 mm and 80 mm, or between 2 cm and 15 cm.

The one or more electrically conducting layer(s) may have an electrically conducting layer length that is able to be stretched at least 20% relative to its relaxed state.

The one or more electrically conducting layer(s) may be stretchable to the same degree as the first elastic support material.

The one or more electrically conducting layer(s) may have an electrically conducting layer length that is defined by the body part such that when the first elastic support material is placed around and/or on the body part and/or on the second elastic support material in contact with the body part, the electrically conducting layer length is pre-stretched at least 20% relative to its relaxed state.

In one embodiment of the device, the one or more electrically conducting layer(s) are separated from each other along the vertical axis.

In another embodiment of the device, the one or more electrically conducting layer(s) are separated from each other along the longitudinal axis, in particularly the one or more electrically conducting layer(s) may be separated from each other along the lateral axis by having a stretchable film between two of said electrically conducting layers. The stretchable film defines that the electric property is the electric capacitance of the stretchable film. The capacitance of the stretchable film is proportional to an area, over which there is an overlap of the two electrically conducting layers, and inverse proportional to the distance between the two electrically conducting layers, i.e. inverse proportional to the thickness of the stretchable film. Thus, the capacitance is also proportional to the length of the electrically conducting layers. Hence, the longer the electrically conducting layers, the greater the capacitance. Thus, by swelling, the length and thereby the circumference increases, and accordingly, the capacitance increases.

In an alternative and/or additionally, the electric property is the resistivity of the electrically conducting layer(s). The resistivity is proportional to the length of the electrically conducting layer and inverse proportional to the cross-sectional area of the electrically conducting layer, i.e. thickness and the width of the electrically conducting layer. Hence, the longer the electrically conducting layers, the greater the capacitance. Thus, by swelling, the length and thereby the circumference increases, and accordingly, the resistivity increases.

A difference between the capacitance and the resistivity in relation to when the one or more electrically conducting layer is stretched, is that the capacitance is influenced by the change in thickness of the stretchable film, whereas the resistivity is influenced by the change in the thickness of the one or more electrically conducting layer.

If the thickness of the one or more electrically conducting layer(s) and the stretchable film may however be deformed in the same manner, there may not be a difference in how the measurement is proportional to the length. On the other hand, a stretchable film may be chosen such that it deforms in a different manner than that of the one or more electrically conducting layer(s), thereby providing advantages in measuring capacitance in comparison to measuring the resistivity, in particular because the capacitance can be made approximately linearly dependent on the length deformation of the one or more electrically conducting layer(s). Several features of the stretchable film are described in the following section.

By using a stretchable film between two layers, and measuring the capacitance, there is provided means for providing a dielectric electroactive polymer (EAP) structure, in particular when the stretchable film is a polymer.

In one embodiment of the present invention, the stretchable film is a polymer that may be made from a material having a resistivity larger than $10^{10}$ Ωcm.

Preferably, the resistivity of the dielectric material is much higher than the resistivity of the electrically conductive layer, preferably at least $10^{14}$-$10^{18}$ times higher.

The film structure may comprise any number of layers of an elastically deformable polymer film, e.g. one, two, three, four, or five layers of the elastically deformable film either adhesively joined or simply stacked above each other to form a laminated structure. The elastically deformable film may particularly be made from a dielectric material which herein is considered to cover any material which can sustain an electric field without conducting an electric current, such as a material having a relative permittivity, which is larger than or equal to 2. It could be a polymer, e.g. an elastomer, such as a silicone elastomer, such as a weak adhesive silicone or in general a material which has elastomer like characteristics with respect to elastic deformation. For example, Elastosil RT 625, Elastosil RT 622, Elastosil RT 601 all three from Wacker-Chemic could be used as a dielectric material.

In the present context the term 'dielectric material' should be interpreted in particular but not exclusively to mean a material having a relative permittivity which is larger than or equal to 2.

In the case that a dielectric material which is not an elastomer is used, it should be noted that the dielectric material should have elastomer-like properties, e.g. in terms of elasticity. Thus, the dielectric material should be deformable to such an extent that the composite is capable of deflecting and thereby pushing and/or pulling due to deformations of the dielectric material.

The film may have a thickness between 10 μm and 200 μm, such as between 20 μm and 150 μm, such as between 30 μm and 100 μm, such as between 40 μm and 80 μm.

In relation a setup with two electrically conducing layers, a first conductor may be attached to the first electrically conductive layer in a first connection point, and the second conductor may be attached to the second electrically conductive layer in a second connection point. The conductor may be formed as an elongated body like a traditional wire or cable. In another embodiment, the conductors may be formed as pouches being circular, oval, or of another shape suitable for establishing the electrically communication with one of the electrodes.

By having a stretchable film as described, in particular a dielectric electroactive polymer, it is clear the one or more electrically conducting layer(s) are configured as an actuator. Actuation is then caused by electrostatic forces between two electrodes which squeeze the polymer. Dielectric elastomers are capable of very high strains and are fundamentally a capacitor that changes its capacitance when a voltage is applied by allowing the polymer to compress in thickness and expand in area due to the electric field.

Thus, by using a stretchable film there is provided a device that is able to work as an artificial muscle.

Elastic Support Material

In one embodiment, the first elastic support material is configured for being attached to the skin of the body part. The first elastic support material may for example comprise cotton, acrylic fibres, be breathable and be water proof.

In most preferred embodiments, the first elastic support material comprises of polyurethane fibres, for example elastene.

In other most preferred embodiments, the first elastic support material is configured with a smooth surface that is defined by its coefficient of friction, wherein the coefficient of friction between the smooth surface and a surface of steel is between 0.2 and 0.4.

The coefficient of friction may be measured using a standard friction test, using for example a commercial system known as the KES system—a system developed by the Hand Evaluation and Standardization Committee of the Textile Machinery Society, Japan. In particular, the coefficient of friction may be measured using the KES-FB4.

The coefficient of friction depends on many factors, including temperature and moisture. Thus, the coefficient of friction as herein referred to may be for textiles that are conditioned at a relative humidity at 65±2% and a temperature of 22±1° C.

Friction tests may involve sliding a probe on the test material with a constant force, whereby a coefficient of friction curve is given by the ratio of the force registered in a transducer (attached to the probe) to the normal force. The mean value of the coefficient of friction is thus the average height of the curve.

Accordingly, the coefficient of friction as referred to herein may be referred to as the kinetic coefficient of friction. Furthermore, the coefficient of friction as referred to herein may be referred to as the mean kinetic coefficient of friction.

It is clear that the coefficient of friction also depends on the probe material. For standardized measurements, the probe is made steel.

However, it may be possible to provide a coefficient of friction measurement of textiles on skin, for example by rubbing a measuring probe with a multi-component force sensor on a part of the skin, whereby the normal and tangential forces can be measured in order to determine the coefficient of friction. It has been found that different parts of the body, i.e. different skin parts of the body, changes the coefficient of friction measurement of a textile. Furthermore, coefficient of friction when measured on skin is very dependent on skin type and varies from person to person, thus making it difficult to provide a standard measurement.

For this reason, a steel probe as used to define the coefficient of friction enables a standardized measurements for coefficient of friction.

As explained herein, the first elastic support material may be in contact with the skin, since it may be the layer of the device that can be in contact with the patient.

The inventors have found that by having the first elastic support material configured with a smooth surface that is defined by its coefficient of friction, wherein the coefficient of friction between the smooth surface and a surface of steel is between 0.2 and 0.4, enables that the device is to be placed on the skin such that the device does not change its placement on the body part. Furthermore, the coefficient of friction between 0.2 and 0.4 as defined above enables that the device is to be placed on the skin such that the device defines a contact surface that is easily adapted to the body part without the first support material being wrinkled, for example by not sticking to the body part.

As explained herein, the first elastic support material may also be in contact with a second elastic material such as a bandage.

The inventors have found that by having the first elastic support material configured with a smooth surface that is defined by its coefficient of friction, wherein the coefficient of friction between the smooth surface and a surface of steel is between 0.2 and 0.4, enables that the device is to adapt to the body part without the support material being wrinkled, for example by not sticking to a second elastic support material such as a bandage.

In other words, the coefficient of friction between 0.2 and 0.4 as defined above, is selected to enable the surface of the first elastic support material to adapt to the body part such that it does not stick to either the body part or a second elastic support material. The inventors have found that this particular coefficient of friction provides an optimal value. If the value was lower, the device would get misplaced. If the value was higher, the device would wrinkle. Thus, the inventors have found that the coefficient of friction between 0.2 and 0.4 as defined above facilitates a very precise measurement of the circumference of the body part.

In a second embodiment, the first elastic support material length, in a relaxed state, is between 15 cm and 85 cm. Thereby should it be configured to fit various body parts of various sizes.

In a third embodiment, the first elastic support material is a circular band configured to fit around a body part. The circular band may be made from the device according to the present invention, for example by sewing the two ends of the first elastic support material together. In other words, the first elastic support material or at least a part of it, may be sewable to form a circular band.

In some embodiments, the first elastic support material or at least a part of it, is gluable. Such an embodiment may provide for the transmitting unit to be attached to the device.

Most preferably, a kit comprises a plurality of devices, each device configured for providing a measure of a circumference of a body part according to the first aspect of the invention. The plurality of devices, may be up to four devices, each device being configured such that the first elastic support material is circular as just described, and each device with different first elastic support material length. In this way, a first device having one circumference, may fit to some patients having swelled legs with a first circumference interval, while another device having a second circumference, may fit to other patients having a second circumference interval. The second circumference may for example be larger than the first circumference interval. In relation hereto, it may also be such that if a patient having the second device, experience a de-swelling, that patient may then be able fit the first device, whereby a more efficient measurement and/or treatment is achieved.

As also described earlier, the elastic support width, in a relaxed state, may be between 1 cm and 15 cm.

The first elastic support material length is able to be stretched at least 20% relative to its relaxed state. By this embodiment there is first of all provided a measurement of the circumference, where the circumference can increase at least 20%, for example if the first support material is attached to the body part such that the first elastic support layer, and thereby also the one or more electrically conducting layer(s), is/are approximately is in a relaxed state. Secondly, there is provided a measurement of the circumference, where the circumference can decrease after the first elastic support material has been placed around the body part and/or the second elastic support material, for example if the one or more electrically conducting layer(s) has/have been pre-stretched up to at least 20% in the process of placing the first elastic support material on the body part and/or the second elastic support material.

In preferred embodiments, the first elastic support material length is able to be stretched up to 250% relative to its relaxed state, such as up to 40%, such as up to 60%, such as up to 80%, such as up to 100%, such as up to 120%, such as up to 150%, or such as up to 200%.

In most preferred embodiments, the first elastic support material is stretchable to the same degree as the one or more electrically conducting layer(s).

Additional Layer

In one embodiment, at least one additional layer located above and/or below the one or more electrically conducting layer(s) is provided, wherein the at least one additional layer is elastic, and wherein the at least one additional layer is configured for being in contact with the first elastic support material, thereby encapsulating the one or more electrically conducting layer(s) in-between the first elastic support material and the at least one additional layer, and such that at least part of the one or more electrically conducting layer(s) is/are able to move relative to the first elastic support material and/or relative to the at least one additional layer. Preferably the at least one additional layer is identical to the first elastic support material.

In yet another embodiment, the at least one additional layer has an additional layer width that, in a relaxed state and along the vertical axis, is between 1 cm and 15 cm.

In a preferred embodiment, the at least one additional layer is stretchable to the same degree as the first support material.

Measuring Unit

As previously described, in one embodiment, deformation in a polymer film, for example due to being stretched, changes the distances between two electrically conductive layers located on opposite surfaces of the film structure. This changes the capacitance, and the deformation can therefore be measured using the measuring unit.

In another embodiment of the device, the measuring unit is further configured for measuring an electric property related to the one or more electrically conducting layer(s), the electric property being related to temperature and/or moisture. For example, this could be achieved by measuring the resistivity of a single electrically conducting layer as it is known that resistivity is for example temperature dependent.

In alternative or additional embodiments, the device further comprises a sensor to measure temperature and/or moisture.

In another alternative or additional embodiment, the device further comprising an accelerometer, for example to be able to monitor the activity of the person wearing the device.

Preferably, the measuring unit may be attached to the first elastic support material.

In some embodiments, the measuring unit may however be detached from the first elastic support material, for example using wired connection to the one or more electrically conducting layer(s).

Transmitting Unit, Receiving Unit and Control Unit

In one embodiment, the methods further comprises a transmitting unit configured for transmitting the measure of the circumference of the body part to a receiving unit. The receiving unit may receive data with the measure of the circumference of the body part by wireless communication and/or by wired communication.

In some embodiments, the receiving unit may comprise a data storing unit. In one embodiment, the data storing unit is a hard drive, for example a portable drive such as a solid state drive, or an optical drive, for example connected via USB in the case of wired communication.

In a preferred embodiment of the device, the data storing unit may also be removably attached to the first elastic support. This may facilitate an integrated solution of the device, but also a solution, where it may be possible to take the data storing unit from the first elastic support material, thereby be able to plug the data storing unit into an external data accessing unit, such as a computer or a handheld device, thereby accessing the data on the data storing unit.

In some embodiments of the device, the transmitting unit and/or the measuring unit and/or the receiving unit are integrated into one unit.

In another preferred embodiment, the receiving unit is detached from the first elastic support. This may for example be of importance, if the device is placed under a bandage, or simply if the receiving unit does not need to be a removably attached unit. For example, the receiving unit may be a computer, a server or a handheld device. By accessing any of these receiving units, it is possible to get access to the data with the measure of the circumference of the body part.

In a most preferred embodiment, the methods further comprises a control unit configured to control the length of the one or more electrically conducting layer(s) along the longitudinal axis, for example by receiving the measure of the circumference of the body part directly from the transmitting unit. The one or more electrically conducting layer(s) may be configured as an actuator, such that when the controller receives input, for example based on the measure of the circumference of the body, the control unit may send an electrical signal to the one or more electrically conducting layer(s), such that the length is shortened. Thus, by having the control unit, the present invention provides for a feed-back mechanism based, i.e. treatment that is based on tightening the first elastic support material further to the body part when it receives instructions based on output from the measuring unit. In other words, the present invention may provide an automatic and self-adaptable support material, for example such as a bandage and/or a compression garments.

EXAMPLES

Example 1

A Device Suitable for the Methods According to the Invention

FIG. 1 shows an example of a device suitable for providing a measure according to the various aspects of the present invention, where it can be seen that the device comprises a first elastic support material 1 configured for being placed around and/or on the body part, the first elastic support material having a first elastic support material length defining an longitudinal axis 2, a first elastic support material width defining a vertical axis 3. There is one or more electrically conducting layer(s) in contact with at least a part of the first elastic support material along at least a part of the longitudinal axis and/or along at least a part of the vertical axis (not to be seen as the layer(s) are under the first elastic support material). In addition, there is one additional layer in contact with the one or more electrically conducting layer(s), i.e. under the first elastic support material, wherein the at least one additional layer is elastic, and wherein the at least one additional layer is configured for preventing moist to be transferred to the one or more electrically conducting layer(s). Thus, the one or more electrically conducting layer(s) cannot be seen as they are embedded between the two layers. A measuring unit is able to be electrically connected to the one or more electrically conducting layer(s), in this case, the measuring unit is detached from the first elastic support material 1, using wired connection 4 to the one or more electrically conducting layer(s). The measuring unit, not shown here, is configured for measuring an electric property related to the one or more electrically conducting layer(s), the electric property being related to the measure of the circumference of the body part. Further, the first elastic support width, defining the vertical axis 3, in a relaxed state, is approximately 5 cm. The first elastic support material is configured for being placed around and/or on the body part by having attachment means 5 in both ends of the longitudinal axis, such that both ends can be attached to each other (here the attachment means are on both sides, so only the attachment means in on end can be seen).

Example 2

Providing Measures for a Predetermined Period

The device as exemplified in Example 1 was applied to a patient suffering from severe leg oedema. Two devices were applied around the leg under a compression bandage at position B and C during a time period of approximately 12 hours as can be seen on the times of measurement in FIGS. 2a and 2b.

Figure 2:
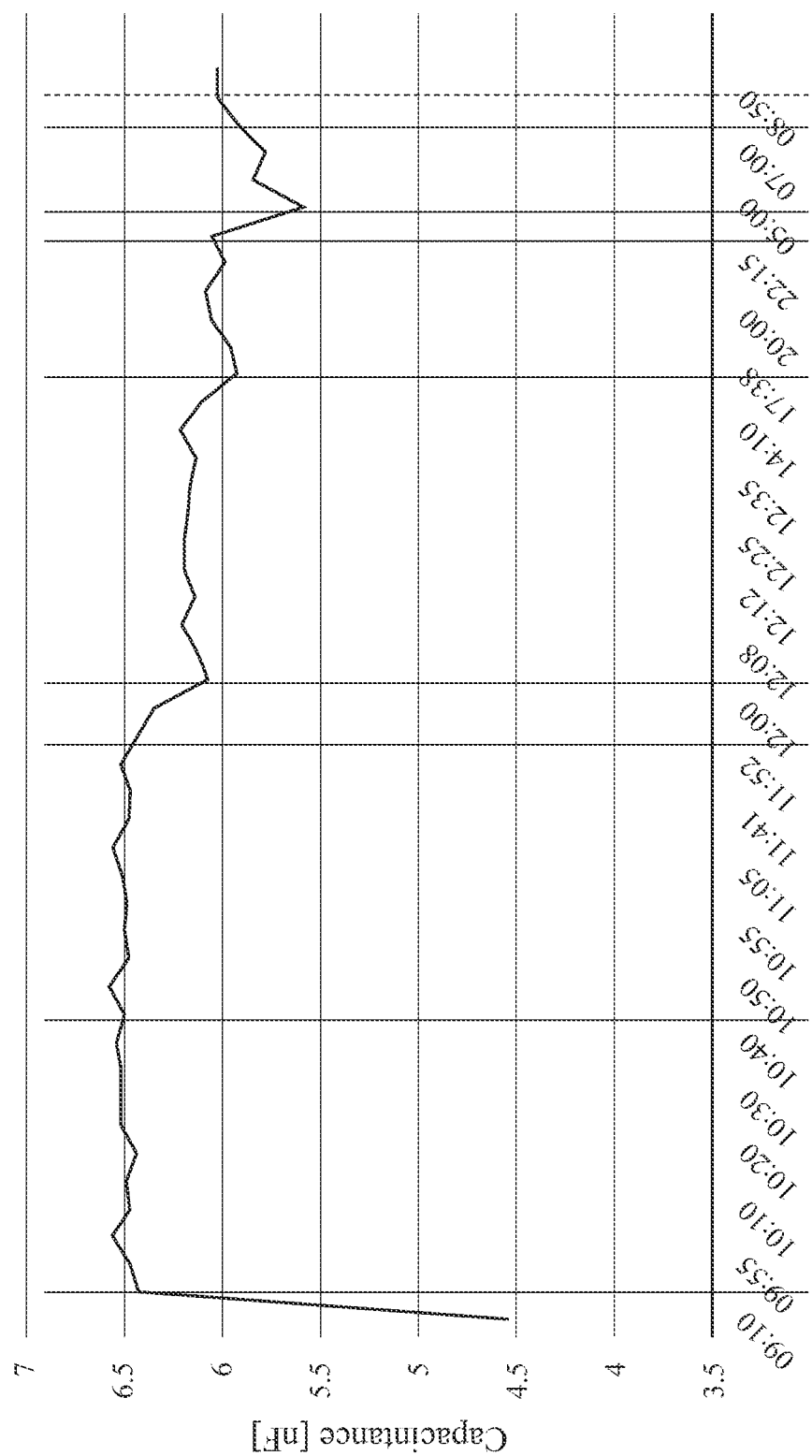
FIG. 2 shows how the electric property, related to the circumference of the leg measured as described in FIG. 1, now in a second position C, changes with time. A time period of approximately 24 hours is shown along the horizontal axis, and the electric property, the capacitance, is shown along the vertical axis. Several measurement points have been indicated along the 24 time period. First is indicated a first measurement 1 where the bandage is applied to the leg. A second measurement 2 is where the patient changes from sitting to walking. A third measurement 3 is where before the bandage is re-applied to the leg and measurement 4 is after the bandage has been re-applied. Measurement 5 is where the patient has the leg in a horizontal position. Measurement 6 is where the patient goes to bed and measurement 7 is where the patient wakes up. At measurement 8, the patient drives a car. At the end, at measurement 9, the measurements are done. As can be seen by comparison of FIG. 1 and FIG. 2, the same leg experiences different changes in circumference at different positions, i.e. B and C. Thus, these two figures show that a more accurate measurement of when the bandage needs to be re-applied, or changed, is provided by having at least two different measurements on at least two different positions.

In this example, the electric property is the capacitance, and it can be seen that in the 12 hour period the capacitance decreases as a function of the leg getting smaller as the swelling decreases. Thus, the capacitance, i.e. the electric property, is able to be related to the measure of the circumference of the body part—in this case the leg. It can be noted, that at night time i.e. from 22:15 to 5:00 when the leg is up, the leg is indeed getting smaller due to the patient lying down. In the night time, the capacitance falls from ca. 6 nF to 5.5 nF. The corresponding reduction in the circumference was from 59 cm to 53 cm. The graphs in FIGS. 2a and 2b shows measurements for each 5 or 10 minutes initially and then measurements for each change, such as changing from sitting to walking slowly. It is apparent that any change in bandage, movement or having the leg in horizontal position during sleep lead to a significant reduction in the swelling and thereby the circumference of the leg, which is documented by the monitoring method. It is also clear when the treatment is not efficient and a new bandage is required since rewrapping the bandage after about 3 hours led to a significant new reduction in the swelling, and before only a modest reduction had been seen at position C. It is also clear that by using two sensors the more information may be provided about the efficiency of the treatment.

Example 3

A Second Measurement from the Measuring Unit

Figure 3A:
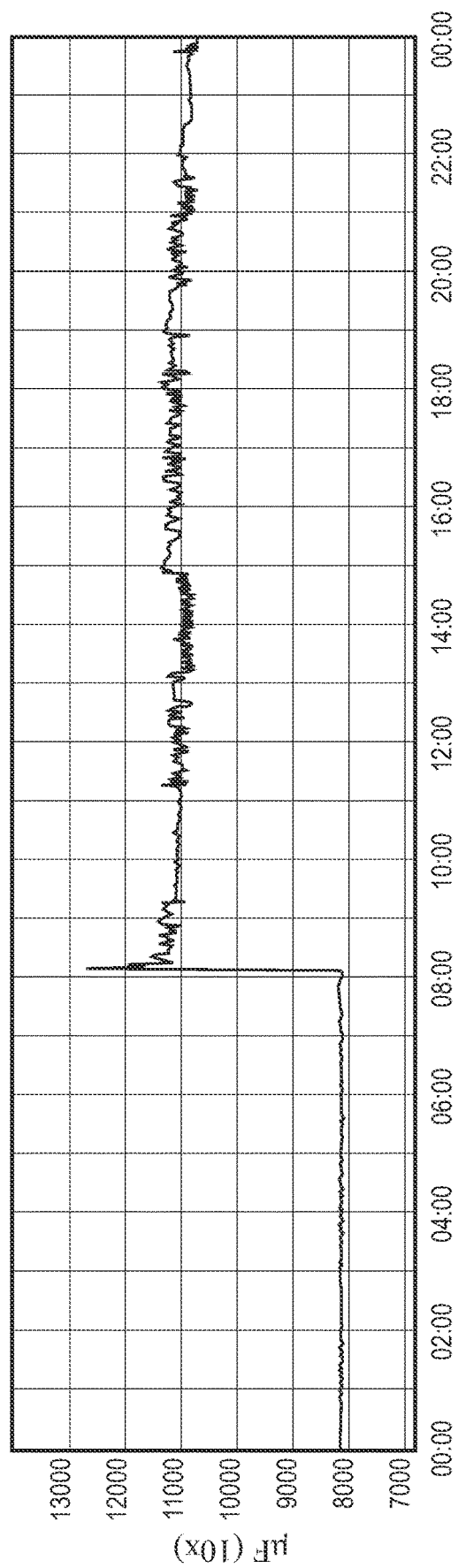
FIG. 3-8 show another example of an electric property being measured using the measuring unit of the device according to the first aspect of the present invention.

FIG. 3A shows an example of an electric property being measured during a time period of 24 hours using the measuring unit of the device according to the first aspect of the present invention.

Figure 3B:
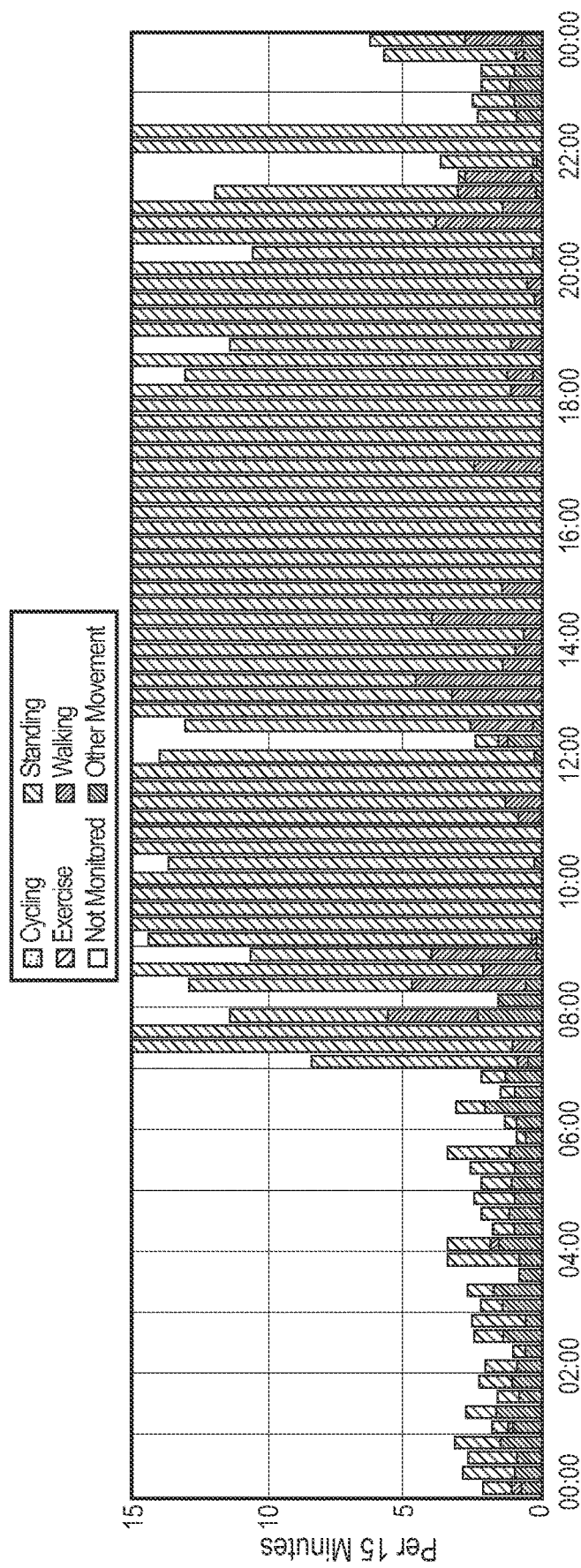

FIG. 3B shows an example of an activity log during the time period of 24 hours, wherein the 25 hours are identical to the 24 hours from FIG. 3A.

Figure 3C:
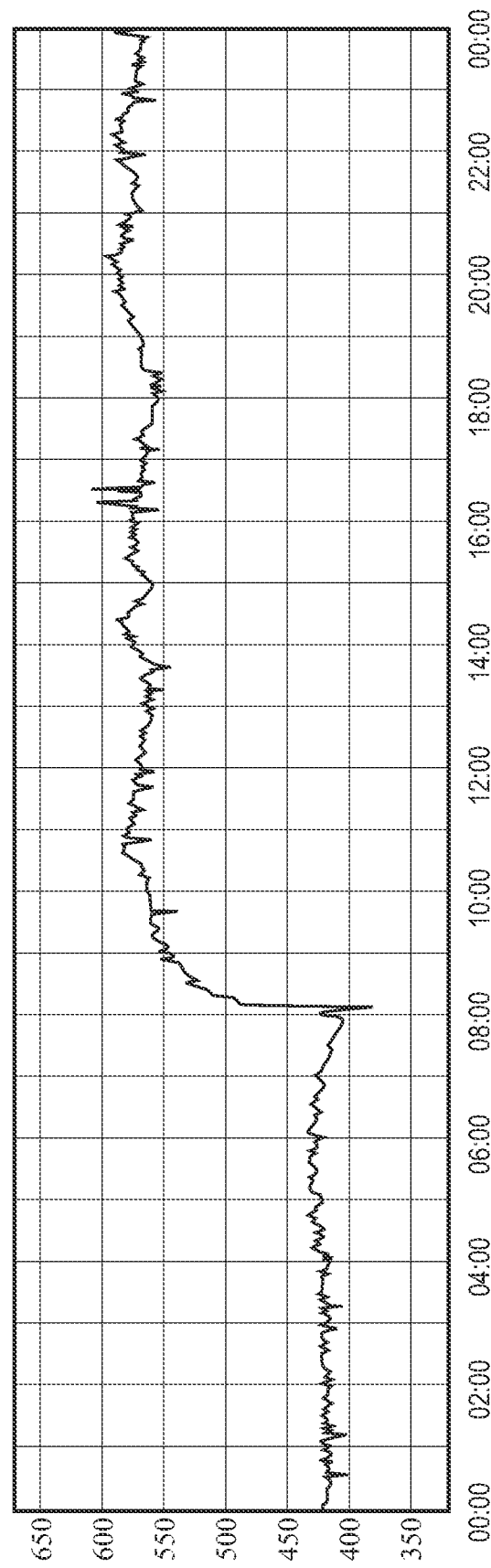
Figure 4A:
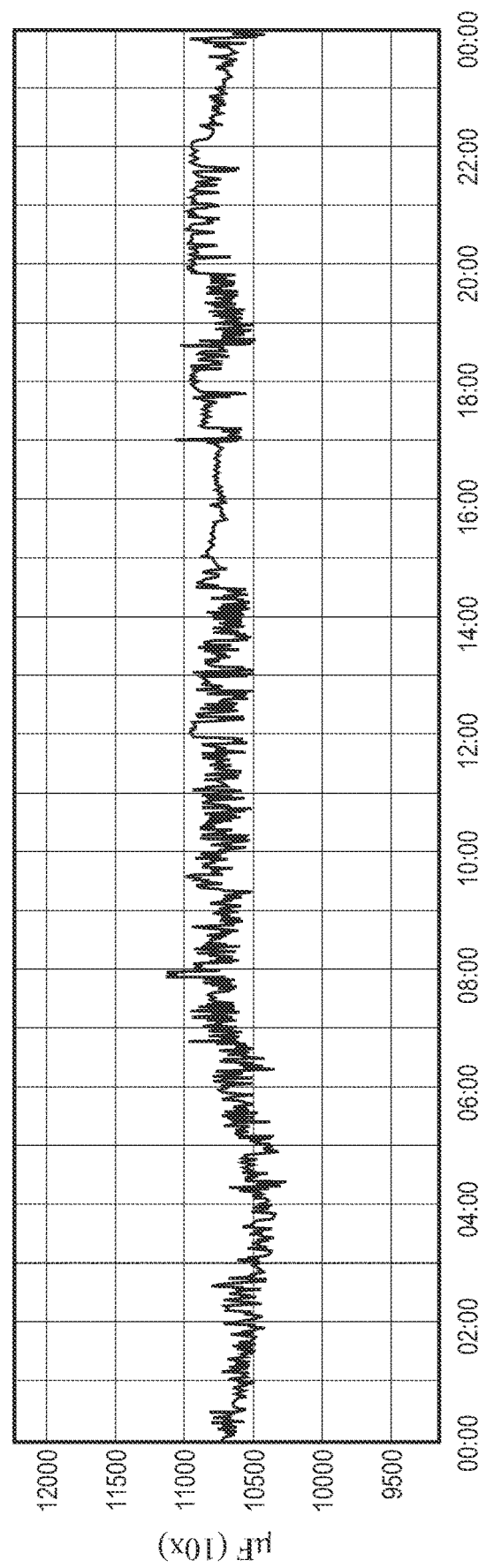
Figure 4B:
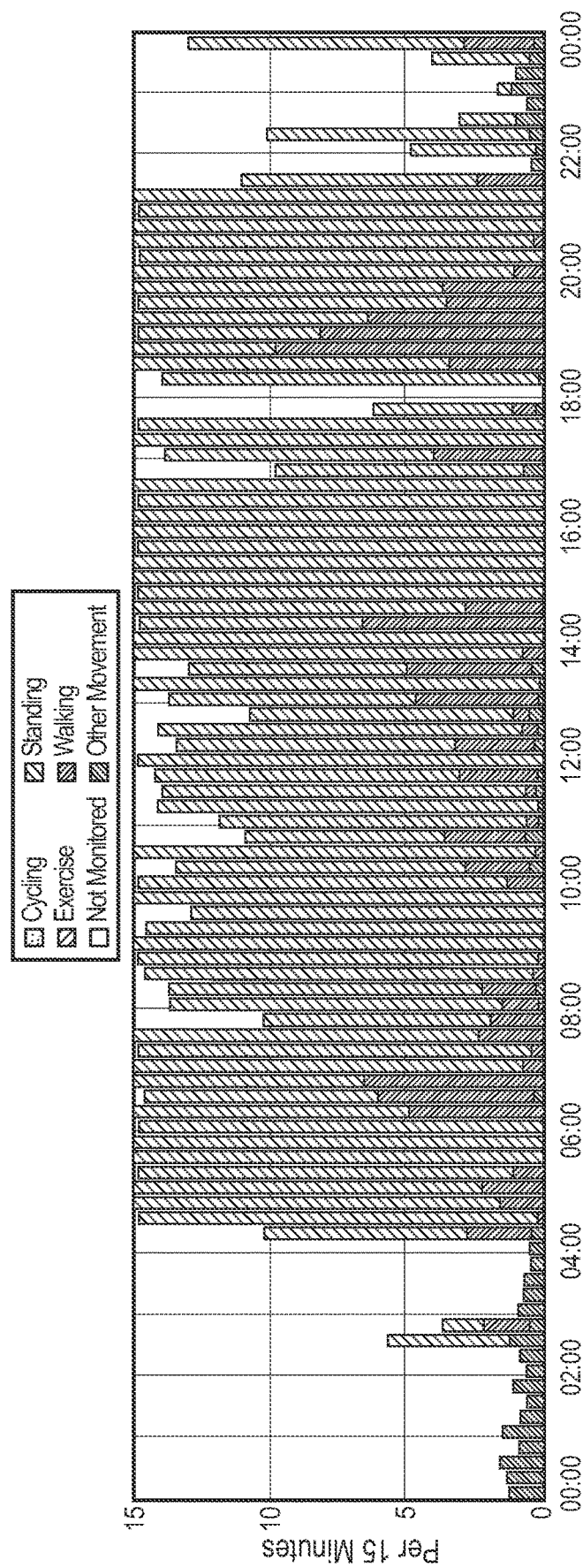
Figure 4C:
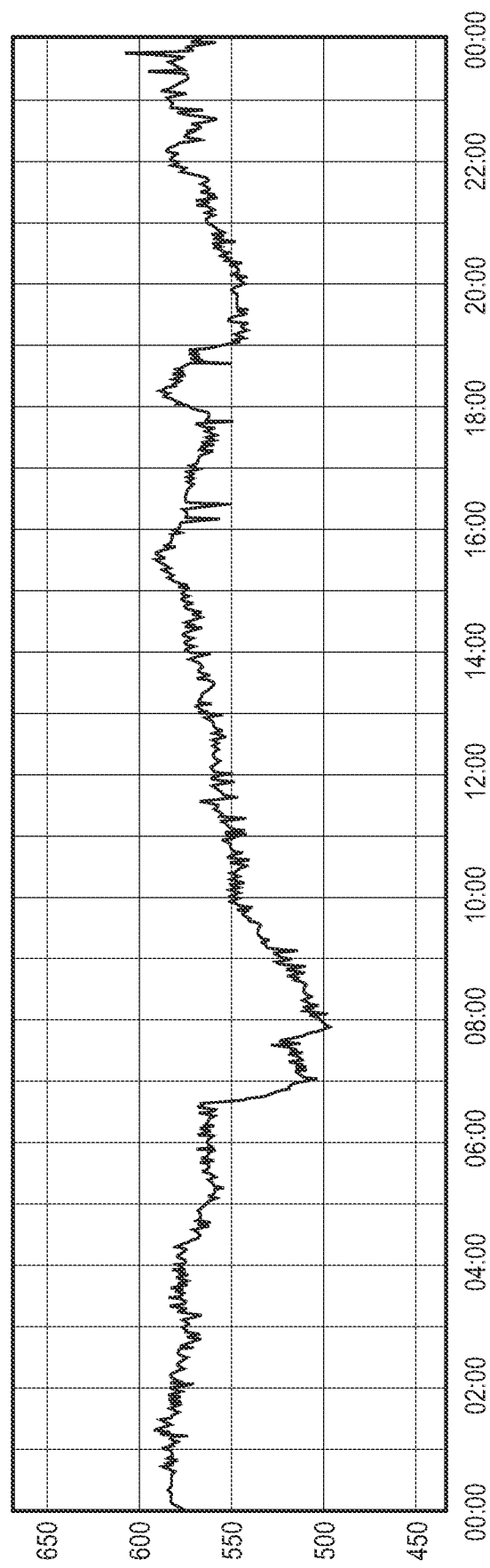
Figure 5A:
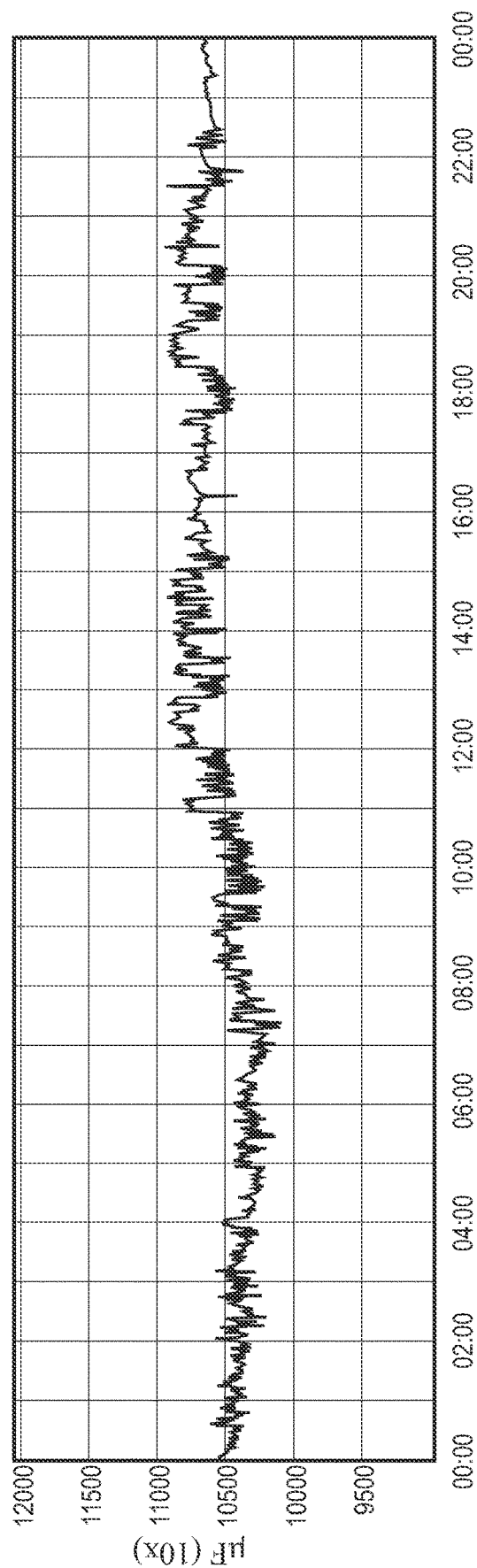
Figure 5B:
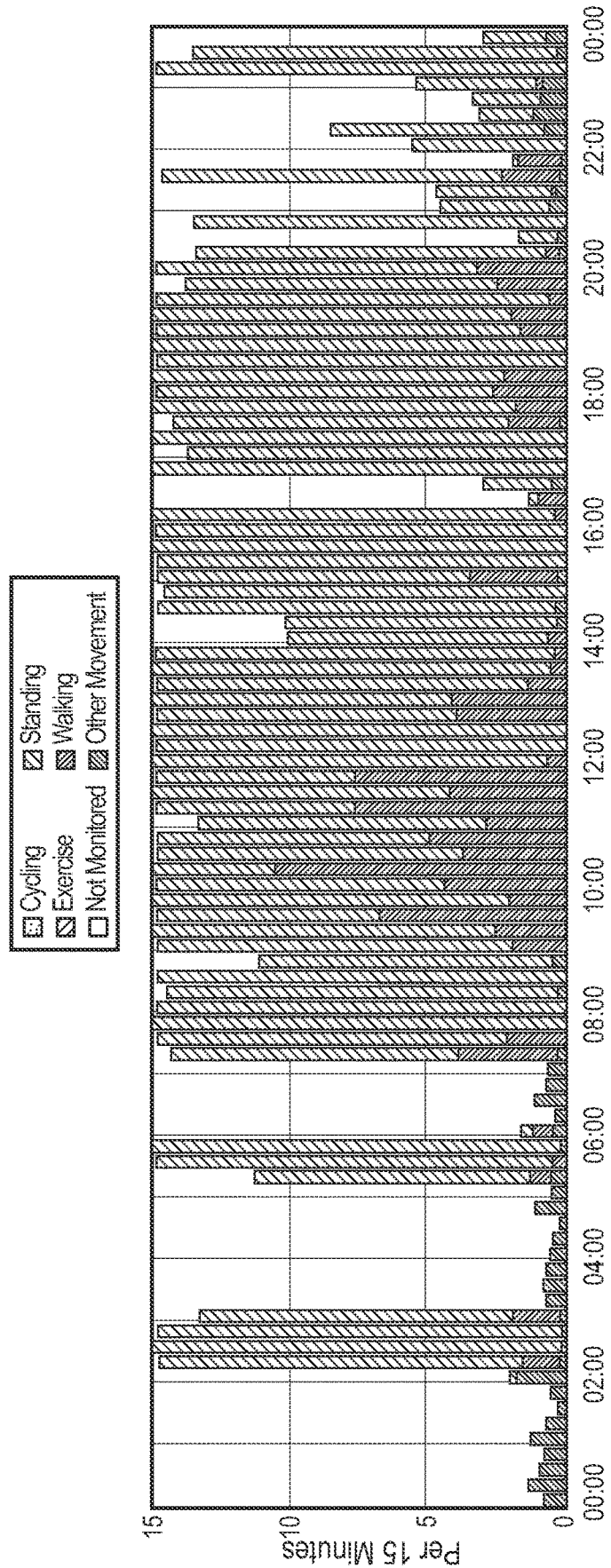
Figure 5C:
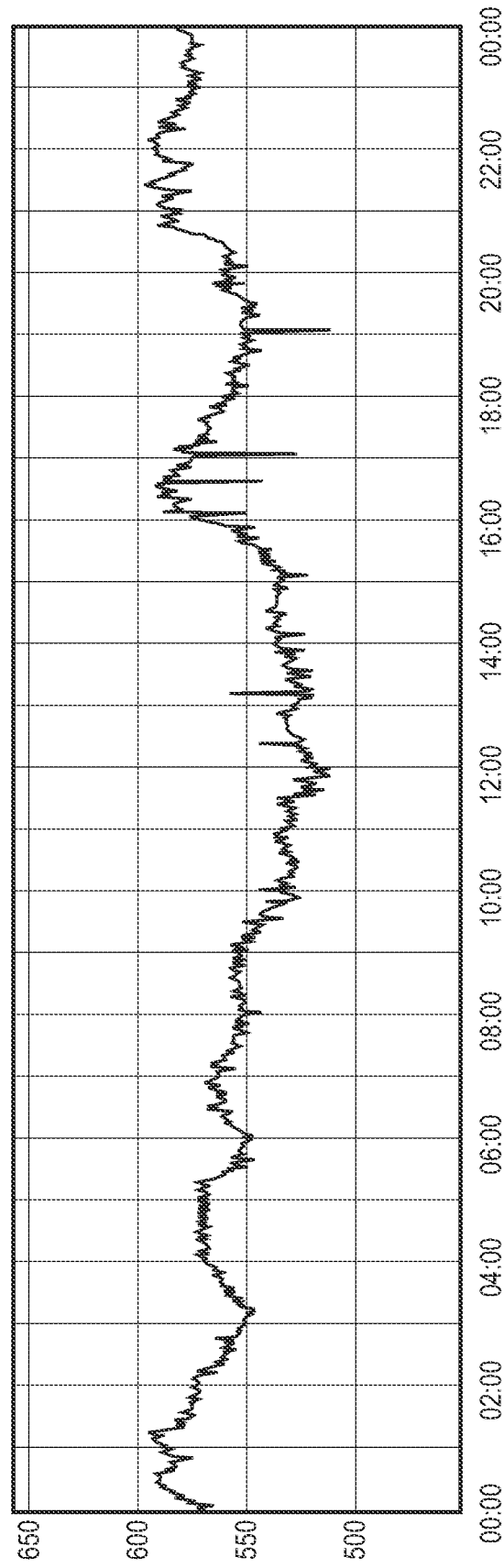
Figure 6A:
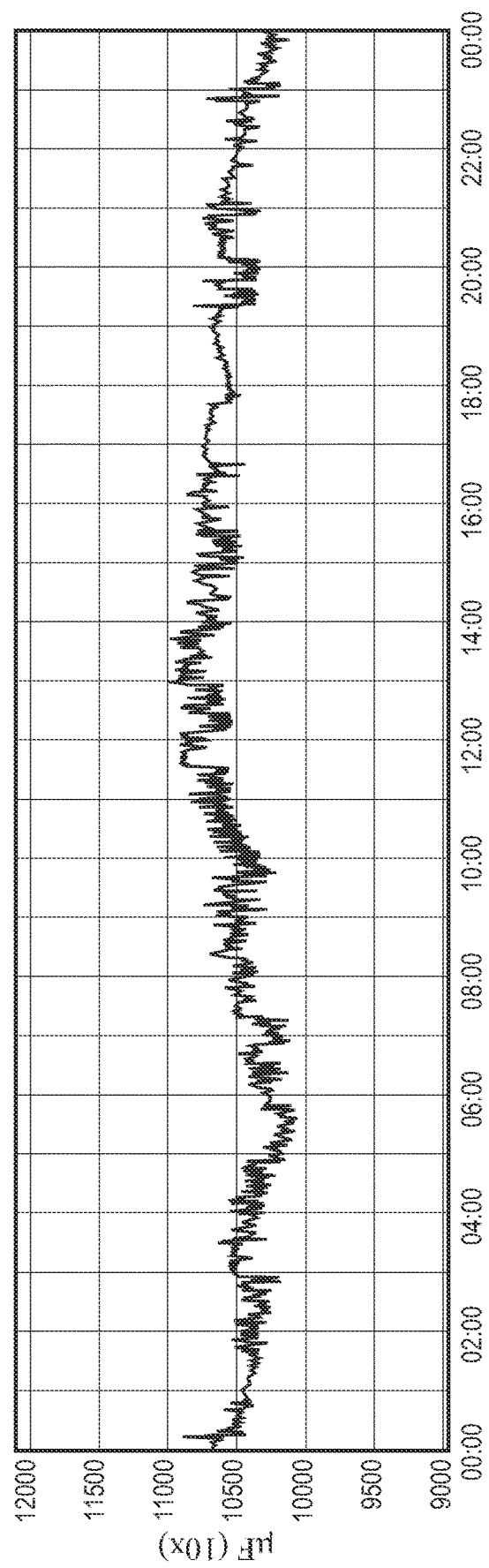
Figure 6B:
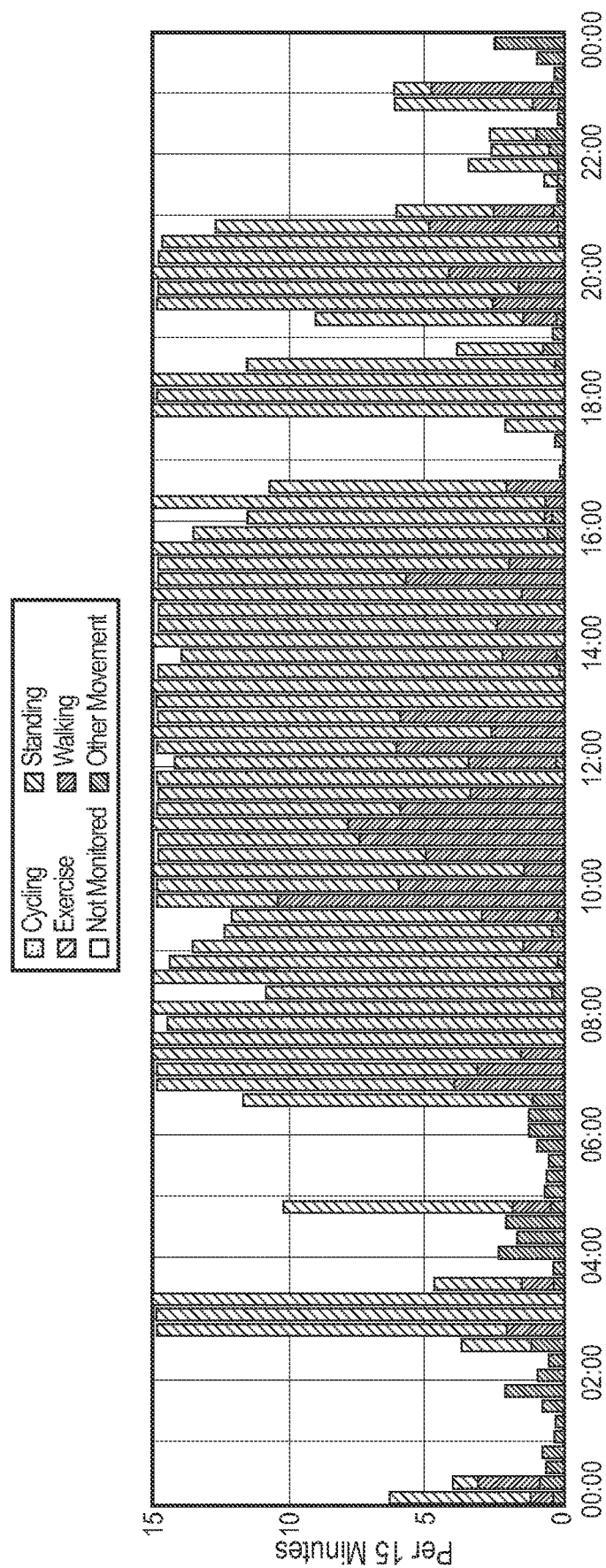
Figure 6C:
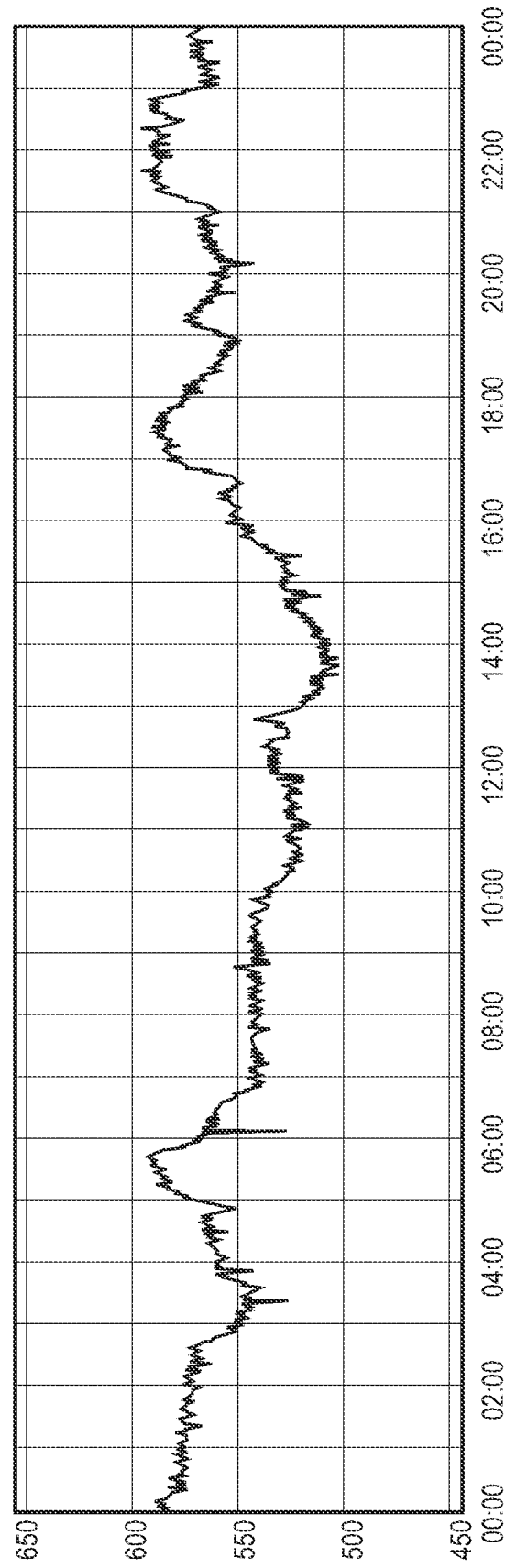
Figure 7A:
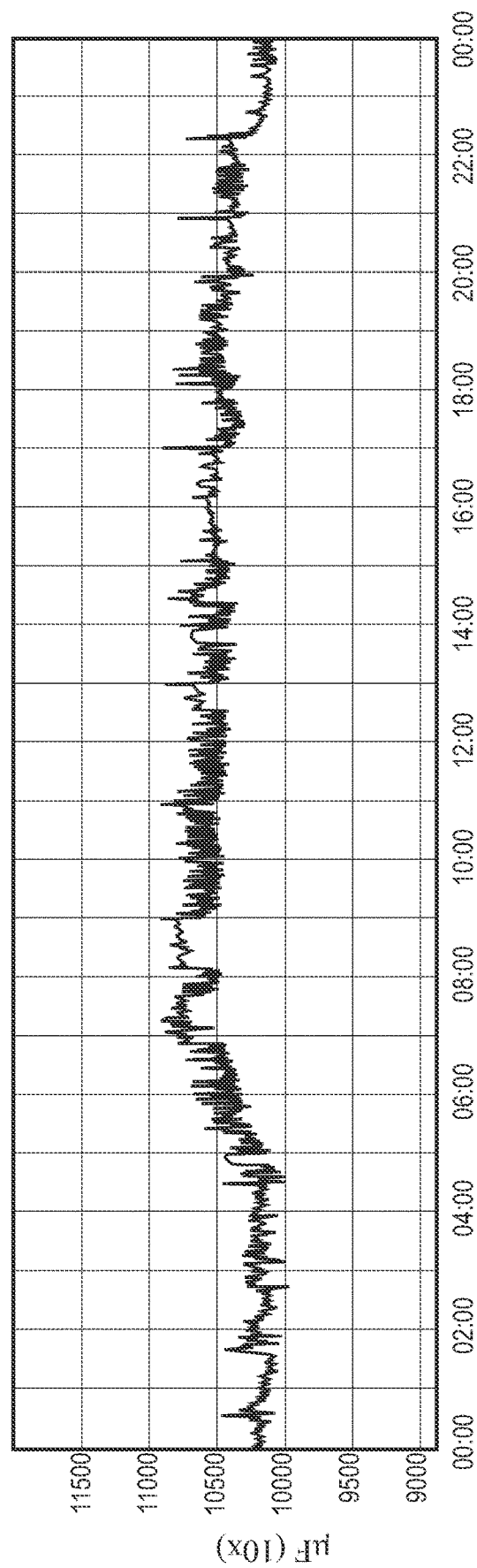
Figure 7B:
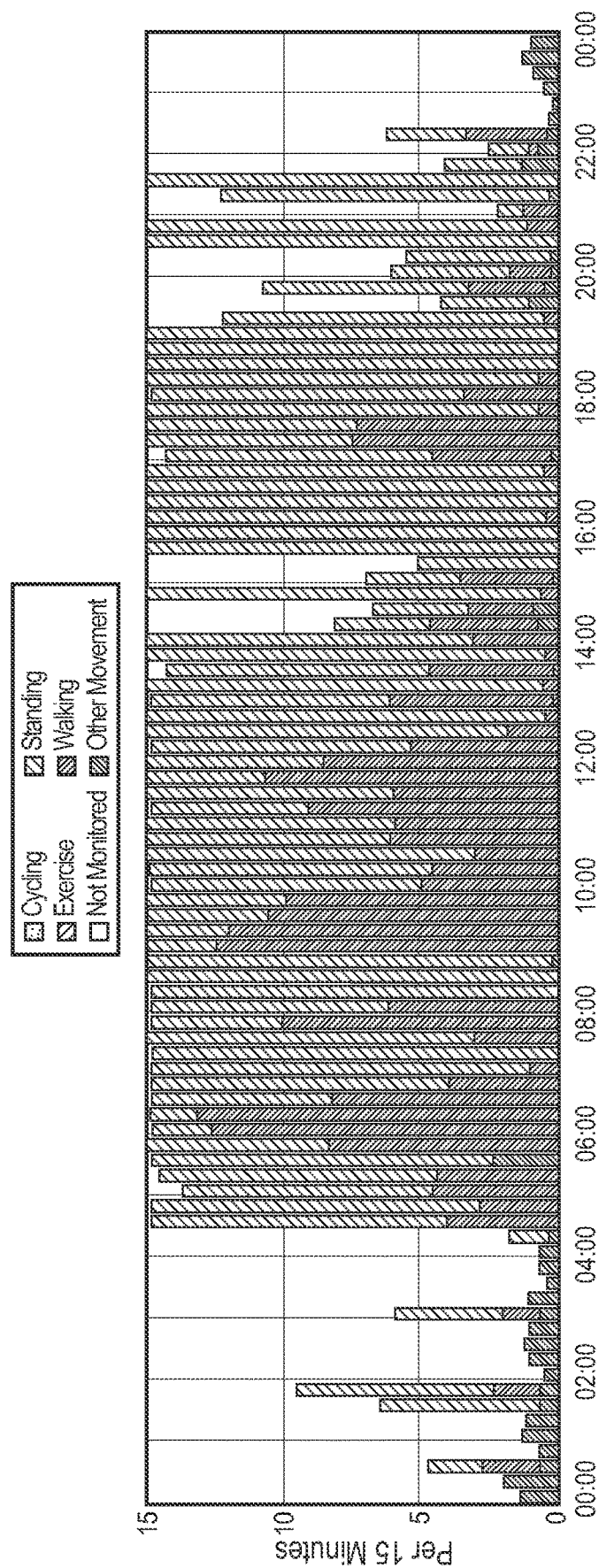
Figure 7C:
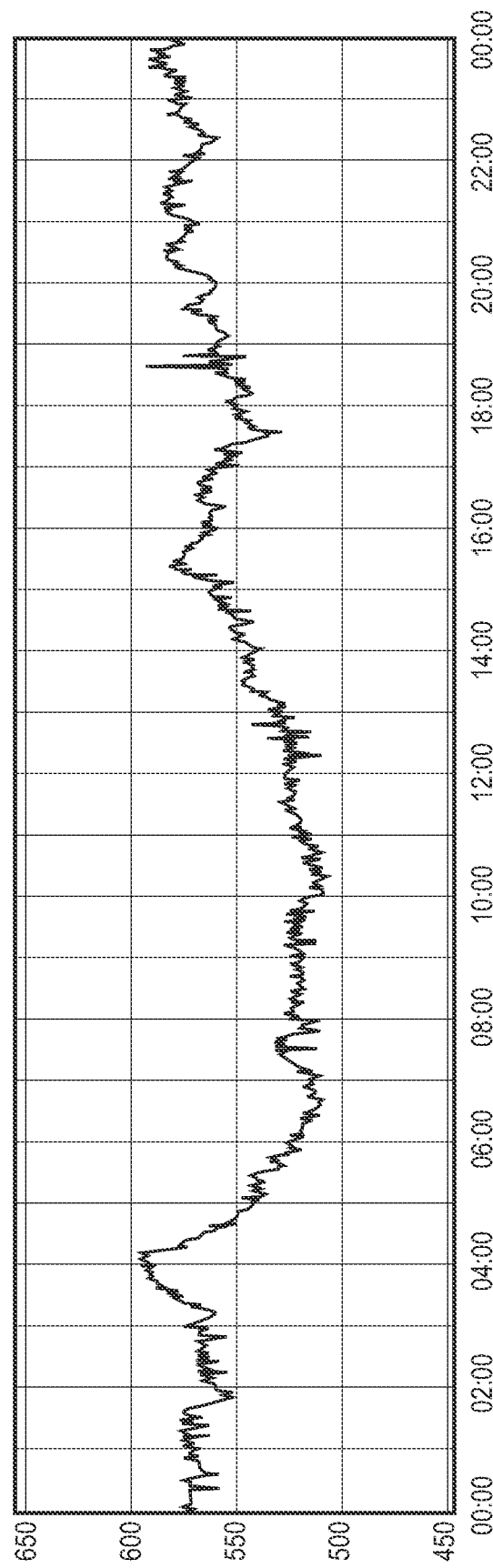
Figure 8A:
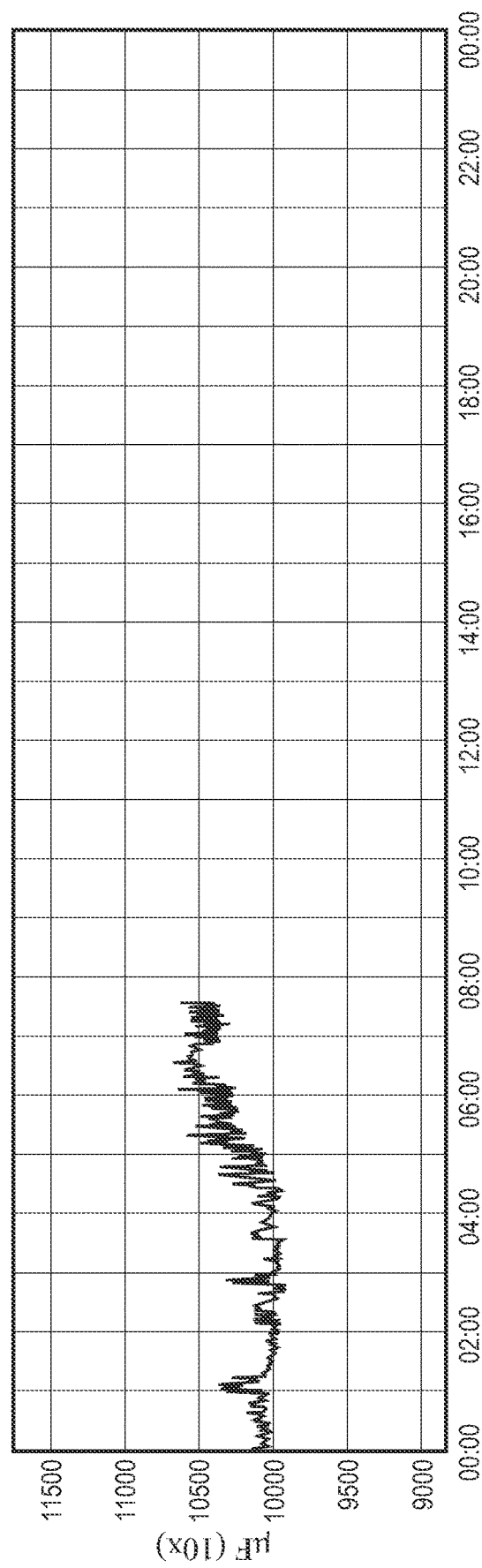
Figure 8B:
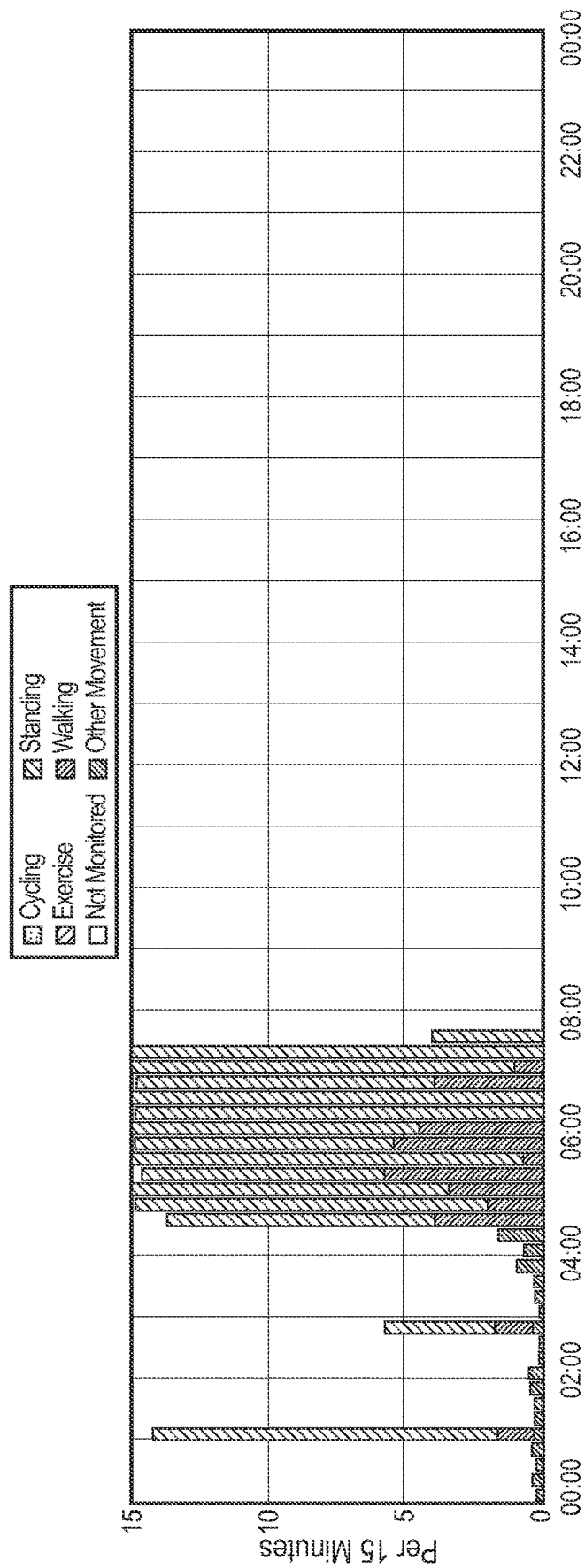
Figure 8C:
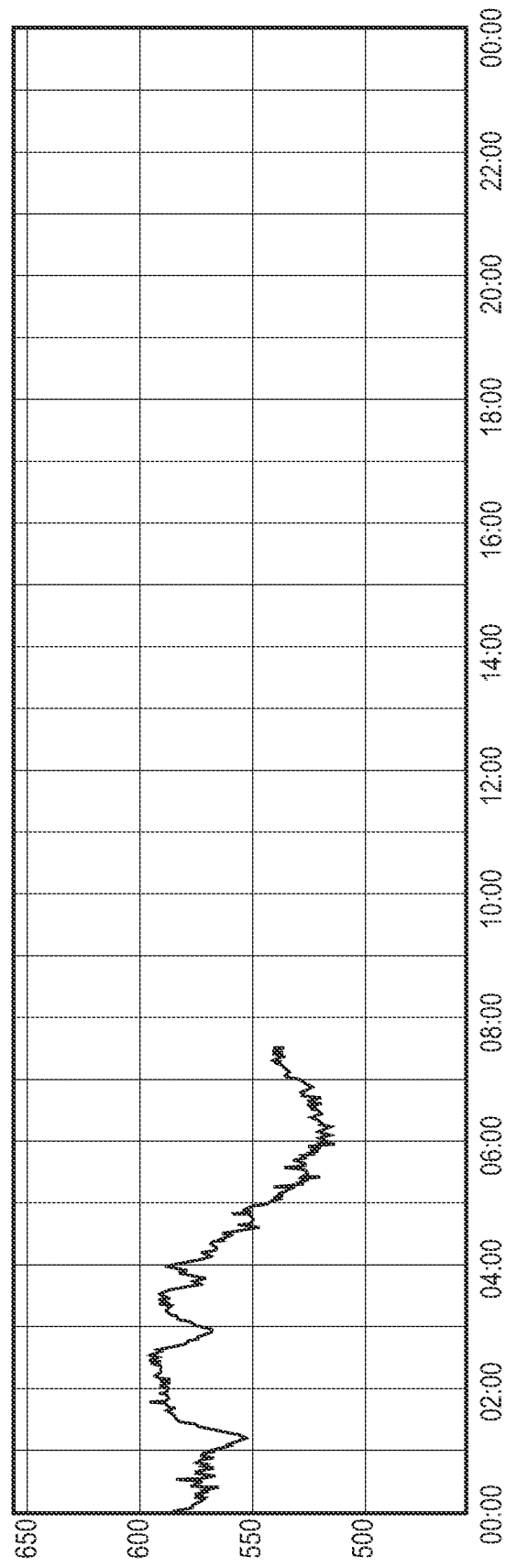

FIG. 3C shows an example of a temperature being measured during the time period of 24 hours, using a sensor to measure temperature, wherein the 25 hours are identical to the 24 hours from FIG. 3A.

The device has been placed around a leg during from the beginning of the morning at around 8:00. In this example, the electric property is the capacitance, and it can be seen that in the period from 8:00 to 0:00, the capacitance decreases as a function of the leg getting smaller as the swelling decreases. Thus, the capacitance, i.e. the electric property, is able to be related to the measure of the circumference of the body part—in this case the leg. In this example, the circumference decreases overnight approximately 3.7 cm.

In the same time period, the patient wearing the device has been told to log his/her activity during the measurement period. In this example, the log is made manually. However, in some embodiments, the device comprises an accelerometer that is configured for automatically logging an activity of the patient wearing the device.

Also in the same time period, the temperature of the patient's leg has been measured as shown in FIG. 3C. The temperature may be related to the activity of the patient and/or as an indication of inflammation in the leg.

Example 4

Further Measurements from the Measuring Unit

FIG. 4-8 show further measurements similar to the measurements as shown in FIG. 3. The FIGS. 3-8 demonstrate that the device has been on an individual for 5 days, including 5 nights. Over the 5 nights, the circumference of the body part, in this case, a leg, has decreased by 6.3 cm. As observed from the FIGS. 3-8, the leg decreases in in circumference during night time, and increases in circumference during day time.

The first night, the circumference decreases from 57 cm to 53.3 cm. The second night, the circumference decreases to 52.4 cm. The third night, the circumference decreases to 52.1 cm. The fourth night, the circumference decreases to 51.6 cm, whereafter a new bandage is applied. The fifth night, the circumference decreases to 50.7 cm.

The invention as provided, enables that the circumference of a body part to be measured. As for the case in relation to the measurements shown in FIG. 3-8, the measurements could be used to determine, when the bandage needed to be changed, for example, as was shown, when the circumference of the leg had decreased by more than 5 cm, indicating that the bandage was no longer optimal for that particular circumference. As was shown, this was happened already after four nights. The present invention provides for a device and method that makes treatment of swelled legs more efficient. Furthermore, the experimental results have demonstrated that de-swelling is not linear. The leg swells during day time and de-swells during night time, however such that the circumference effectively decreases over several days and nights. The invention has thus provided insight into treatment of swelled legs, as has not been possible before. Accordingly, not only is a novel device disclosed herein. Novel treatments are also achieved by the use of the device as described herein.

Example 5

Another Embodiment of the Device

Figure 9:
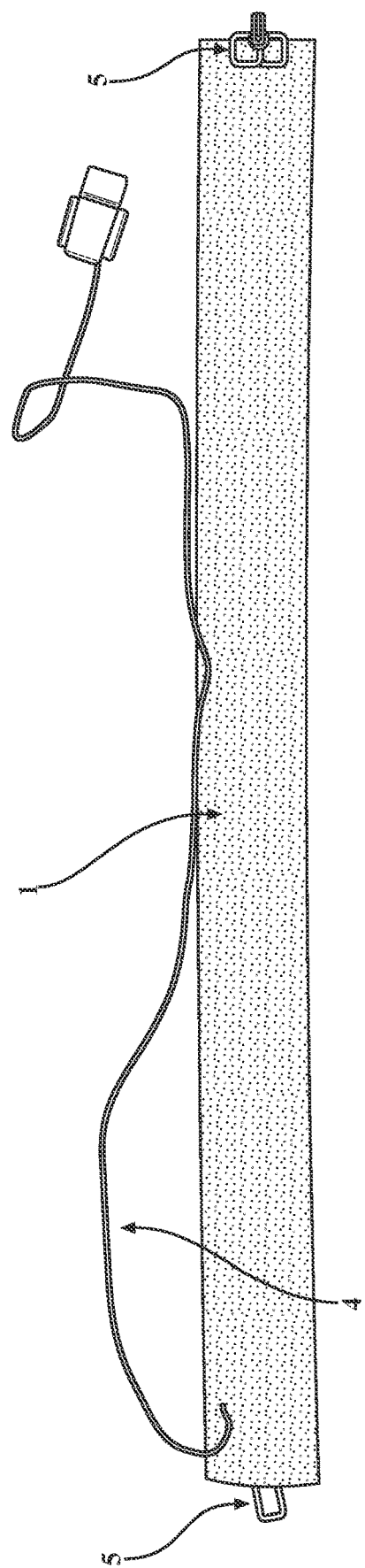
FIG. 9-10 show other embodiments of the device according to the first aspect of the present invention.

FIG. 9 shows another example of the device according to the first aspect of the present invention, where it can be seen that the device comprises a first elastic support material 1 configured for being placed around and/or on the body part, the first elastic support material having a first elastic support material length defining an longitudinal axis 2 (the axis is not shown here), a first elastic support material width defining a vertical axis 3 (the axis is not shown here). There is one or more electrically conducting layer(s) encapsulated between two elastic layers. Thus, the one or more electrically conducting layer(s) cannot be seen as they are between two layers. A measuring unit is able to be electrically connected to the one or more electrically conducting layer(s), in this case, the measuring unit is detached from the first elastic support material 1, using wired connection 4 to the one or more electrically conducting layer(s). The measuring unit, not shown here, is configured for measuring an electric property related to the one or more electrically conducting layer(s), the electric property being related to the measure of the circumference of the body part. In this example, the first elastic support material 1 comprises a surface texture adopted with a roughness similar to a material made of polyurethane fibres (the first elastic support material is made of polyurethane fibres) so that the first elastic support material stays in place once the first elastic support material has been placed around and/or on the body part. Further, the first elastic support width, defining the vertical axis 3, in a relaxed state, is approximately 1.5 cm. The first elastic support material is configured for being placed around and/or on the body part by having attachment means 5 in both ends of the longitudinal axis, such that both ends can be attached to each other.

Example 6

Another Embodiment of the Device with a Measuring Unit

Figure 10:
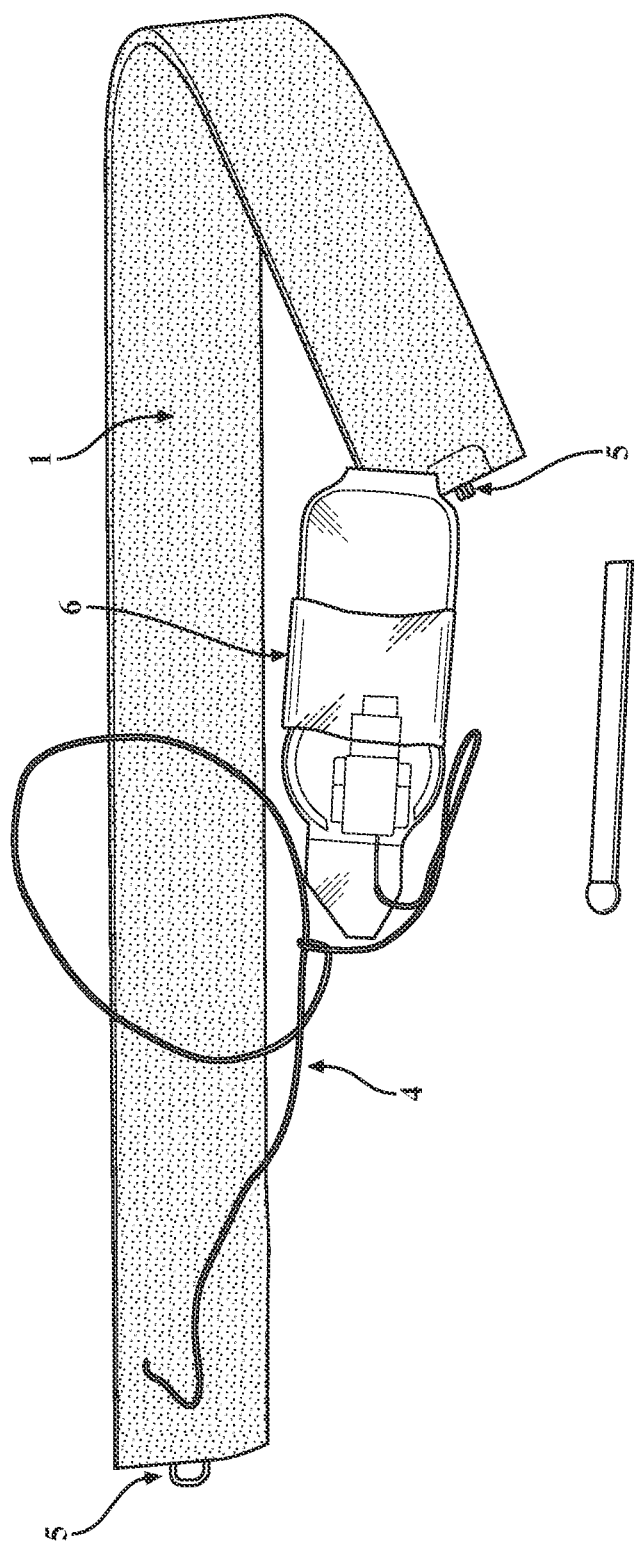

FIG. 10 shows another example of the device according to the first aspect of the present invention, now including a measuring unit 6, where it can be seen that the device comprises a first elastic support material 1 configured for being placed around and/or on the body part, the first elastic support material having a first elastic support material length defining an longitudinal axis (2) (the axis is not shown here), a first elastic support material width defining a vertical axis 3 (the axis is not shown here). There is one or more electrically conducting layer(s) encapsulated between two elastic layers. Thus, the one or more electrically conducting layer(s) cannot be seen as they are between two layers. A measuring unit is able to be electrically connected to the one or more electrically conducting layer(s), in this case, the measuring unit is detached from the first elastic support material 1, using wired connection 4 to the one or more electrically conducting layer(s). The measuring unit 6, now shown here, is configured for measuring an electric property related to the one or more electrically conducting layer(s), the electric property being related to the measure of the circumference of the body part. In this example, the first elastic support material 1 comprises a surface texture adopted with a roughness similar to a material made of polyurethane fibres (the first elastic support material is made of polyurethane fibres) so that the first elastic support material stays in place once the first elastic support material has been placed around and/or on the body part. Further, the first elastic support width, defining the vertical axis 3, in a relaxed state, is approximately 1.5 cm. The first elastic support material is configured for being placed around and/or on the body part by having attachment means 5 in both ends of the longitudinal axis, such that both ends can be attached to each other.

The invention claimed is:

1. A method for determining an efficiency of a compression bandaging, said method comprising:
   on a body part having the compression bandaging, wherein the bandaging comprises at least one sensor under, within or over said bandaging, each sensor comprising;
      one or more electrically conducting layer(s) on or around at least a part of said body part, wherein the electrically conducting layer(s) is/are stretchable;
      a measuring unit that is electrically connected to the one or more electrically conductive layer(s), wherein the measuring unit is configured for measuring a capacitance of the one or more electrically conducting layer(s), wherein the capacitance is indicative of and proportional to a length of the one or more electrically conducting layer(s) and related to a measure of a circumference of the body part;
   registering a plurality of measures of the circumference of the body part during a predetermined period using the measured capacitance indicative of the length of the one or more electrically conducting layer(s),
   determining that the compression bandaging is efficient when the circumference of the body part has decreased below a predetermined circumference cutoff value or the decrease of the circumference of the body part is above a predetermined decrease cutoff value after said predetermined period.

2. The method according to claim 1, wherein the predetermined period is at least 12 hours.

3. The method according to claim 1, wherein the predetermined decrease cutoff value is at least 0.5 to 3.0 cm.

4. The method according to claim 1, wherein the sensor comprises a first elastic support material configured for being placed around or on the body part or on a second elastic support material in contact with the body part, the first elastic support material having a first elastic support material length defining a longitudinal axis, a first elastic support material width defining a horizontal axis and a first elastic support material thickness defining a lateral axis.

5. The method according claim 1, wherein the one or more electrically conducting layer(s) has/have an electrically conducting layer length that is able to be stretched at least 20% relative to a relaxed state of the one or more electrically conducting layers.

6. The method according to claim 1, further comprising a transmitting unit configured for transmitting the measures of the circumference of the body part to a receiving unit.

7. The method according to claim 6, wherein the receiving unit comprises a control unit configured to control a width of the one or more electrically conducting layer(s) along a longitudinal direction by sending an electrical signal to the one or more electrically conducting layer(s).

8. The method according to claim 1, wherein the sensor further comprises one or more non-elastic support material(s) extending from the one or more electrically conductive layer(s) or from the first elastic support material along a longitudinal direction, or along a horizontal direction.

9. The method according to claim 4, wherein the first elastic support material is configured for being attached to a skin of the body part.

10. The method according to claim 1, wherein the measuring unit is further configured for measuring a further electric property related to the one or more electrically conducting layer(s), the further electric property being related to temperature or moisture.

11. The method according to claim 1, wherein the sensor further comprises a sensor to measure temperature or moisture.

12. The method according to claim 1, further comprising at least one additional layer in contact with the one or more electrically conducting layer(s), wherein the at least one additional layer is elastic, and wherein the at least one additional layer is configured for preventing moisture to be transferred to the one or more electrically conducting layer(s).

* * * * *